(12) United States Patent
Stofer et al.

(10) Patent No.: US 7,344,505 B2
(45) Date of Patent: Mar. 18, 2008

(54) BARRIERS AND METHODS FOR PRESSURE MEASUREMENT CATHETERS

(75) Inventors: Alyse Renee Stofer, Woodbury, MN (US); Lynn Marlo Zwiers, Lino Lakes, MN (US)

(73) Assignee: Transoma Medical, Inc., Arden Hills, MN (US)

( * ) Notice: Subject to any disclaimer, the term of this patent is extended or adjusted under 35 U.S.C. 154(b) by 510 days.

(21) Appl. No.: 10/272,489

(22) Filed: Oct. 15, 2002

(65) Prior Publication Data

US 2004/0073122 A1    Apr. 15, 2004

(51) Int. Cl.
*A61B 5/00* (2006.01)
*A61B 5/02* (2006.01)

(52) U.S. Cl. .......... 600/561; 600/30; 600/486

(58) Field of Classification Search .......... 600/311, 600/466–471, 486, 561, 587–594; 604/505, 604/100.01; 523/212–216; 524/493, 492, 524/731; 528/31–43; 427/2.1, 230, 2.11–12, 427/2.28, 2.3
See application file for complete search history.

(56) References Cited

U.S. PATENT DOCUMENTS

| | | | |
|---|---|---|---|
| 3,832,253 A * | 8/1974 | Di Palma et al. .......... 156/86 |
| 3,847,848 A * | 11/1974 | Beer .......... 523/213 |
| 4,196,731 A * | 4/1980 | Laurin et al. .......... 600/435 |
| 4,549,879 A * | 10/1985 | Groshong et al. .......... 604/247 |
| 4,753,640 A * | 6/1988 | Nichols et al. .......... 604/247 |
| 4,755,554 A * | 7/1988 | Itoh et al. .......... 524/588 |
| 4,846,191 A * | 7/1989 | Brockway et al. .......... 600/561 |
| 5,061,481 A * | 10/1991 | Suzuki et al. .......... 424/63 |
| 5,431,628 A * | 7/1995 | Millar .......... 604/100.01 |
| 5,487,760 A | 1/1996 | Villafana |
| 5,519,082 A * | 5/1996 | Yoshino .......... 524/493 |
| 5,535,752 A | 7/1996 | Halperin et al. |
| 5,810,735 A | 9/1998 | Halperin et al. |
| 5,902,248 A * | 5/1999 | Millar et al. .......... 600/485 |

(Continued)

OTHER PUBLICATIONS

Brockway et al., "A new method for continuous chronic measurement and recording of blood pressure, heart rate and activity in the rat via radio-telemetry" *Clinical and Experimental Hypertension* (1991) A13(5): 885-895.

(Continued)

*Primary Examiner*—Charles A. Marmor, II
*Assistant Examiner*—Patricia C Mallari
(74) *Attorney, Agent, or Firm*—Fish & Richardson P.C.

(57) ABSTRACT

Methods and apparatus of the present invention provide viscoelastic barrier materials for use as barriers in devices such as pressure measurement catheters. Improved barrier materials sometimes include at least one barrier material precursor combined with an amount of a softener. In other embodiments, two barrier material precursor components are combined without a softener to provide a fully cross-linked barrier material having certain softness characteristics. In various embodiments, a softener may be dimethyl silicone oil and may be combined with a barrier material precursor in an amount of between about 25% and about 45% by weight, relative to the final barrier material. Once a viscoelastic barrier material is prepared, it may be placed in a pressure transmission catheter or similar device, for example by injecting the gel into a lumen of the catheter via a syringe. Barrier materials of the present invention have one or more advantageous properties, such as a desired softness, full cross-linking, resistance to washout from a catheter, enhanced stability and/or the like.

51 Claims, 10 Drawing Sheets

U.S. PATENT DOCUMENTS

| | | | |
|---|---|---|---|
| 5,904,708 A | | 5/1999 | Goedeke |
| 5,948,539 A | * | 9/1999 | Paulsen et al. ............. 428/447 |
| 5,993,395 A | * | 11/1999 | Shulze ....................... 600/488 |
| 6,019,729 A | * | 2/2000 | Itoigawa et al. ............ 600/488 |
| 6,033,366 A | | 3/2000 | Brockway et al. |
| 6,053,873 A | | 4/2000 | Govari et al. |
| 6,080,605 A | * | 6/2000 | Distefano et al. ........... 438/126 |
| 6,203,898 B1 | * | 3/2001 | Kohler et al. ............... 428/339 |
| 6,296,615 B1 | | 10/2001 | Brockway et al. |
| 6,413,536 B1 | * | 7/2002 | Gibson et al. .............. 424/423 |
| 6,423,322 B1 | * | 7/2002 | Fry ............................ 424/401 |
| 6,857,932 B2 | * | 2/2005 | Chen ........................... 450/38 |
| 2001/0037067 A1 | | 11/2001 | Tchou et al. |
| 2002/0013614 A1 | | 1/2002 | Thompson |
| 2002/0028999 A1 | | 3/2002 | Schaldach et al. |
| 2002/0077553 A1 | | 6/2002 | Govari et al. |
| 2002/0077554 A1 | | 6/2002 | Schwartz et al. |
| 2002/0077671 A1 | | 6/2002 | Govari et al. |
| 2002/0091332 A1 | | 7/2002 | Bombardini |
| 2002/0095196 A1 | | 7/2002 | Linberg |
| 2002/0099302 A1 | | 7/2002 | Bardy |
| 2002/0115939 A1 | | 8/2002 | Mulligan et al. |
| 2002/0120200 A1 | * | 8/2002 | Brockway et al. .......... 600/488 |

OTHER PUBLICATIONS

Sato et al., "Evaluation of a new method using telemetry for monitoring the left ventricular pressure in free-moving rates" *Journal of Pharmacological and Toxicological Methods* (1994) 31(4):191-198.

Van Den Buuse, "Circadian rhythums of blood pressure, heart rate, and locomotor activity in spontaneously hypertensive rats as measured with radio-telemetry" *Physiology & Behavior* (1994) 55(4):783-787.

\* cited by examiner

*Fig.1D*
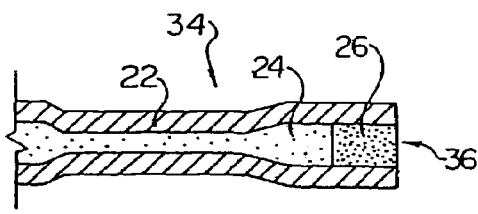
*Fig.1E*
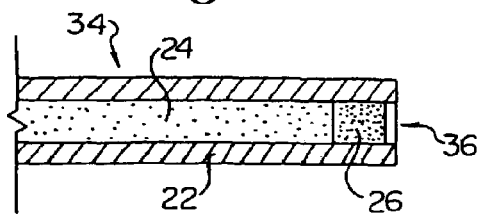
*Fig.1F*
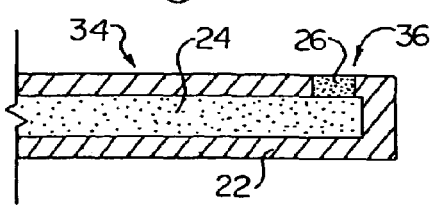
*Fig.1G*
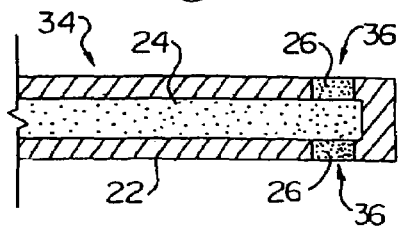
*Fig.1H*
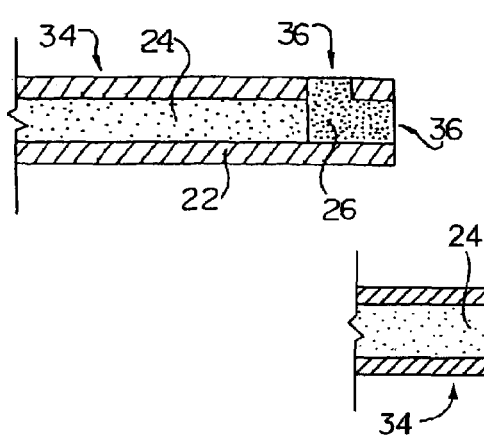
*Fig.1I*
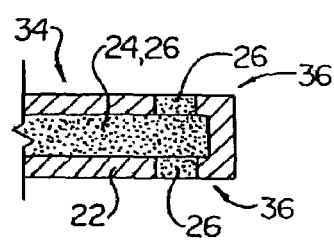
*Fig.1J*
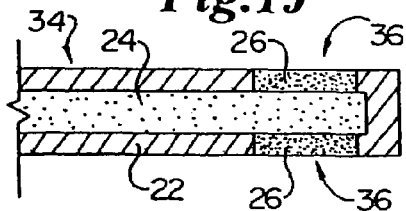
*Fig.1K*
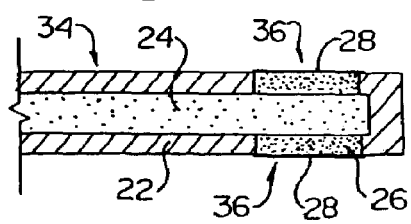
*Fig.1L*
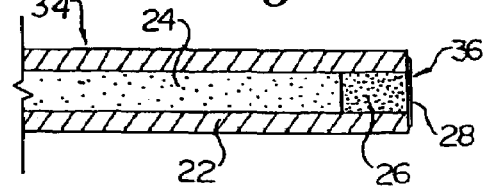
*Fig.1M*
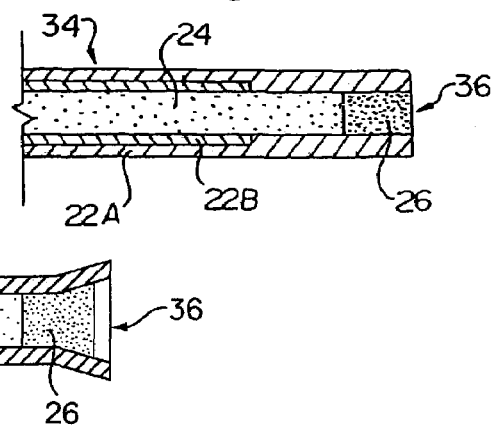
*Fig. 1N*

BARRIERS AND METHODS FOR PRESSURE MEASUREMENT CATHETERS

BACKGROUND OF THE INVENTION

The present invention relates generally to medical devices and methods. More specifically, the invention relates to improved barriers for use in pressure measurement catheters, and methods for making and using the improved barriers.

Implantable pressure measurement devices such as pressure measurement catheters may be used in a wide variety of contexts to measure many types of pressures in human patient care, veterinary or research environments. Pressure measurement catheters may be used, for example, to measure pressures in a human or animal including endocardial, arterial, venous, cerebral, intraocular, urinary, intrauterine, penile, thoracic cavity and various other vascular or tissue pressures. Measurement of bodily pressures using implantable catheter devices may be equally useful in patient care and research settings. For example, use of pressure measurement catheters in various research settings is described in U.S. Pat. No. 4,846,191 to Brockway et al., the disclosure of which is hereby incorporated by reference.

In one context, pressure measurement catheters are used to measure endocardial pressure, such as left ventricular pressure. One example of such catheters is described in U.S. patent application Ser. No. 10/077,566, filed Feb. 15, 2002, entitled DEVICES, SYSTEMS AND METHODS FOR ENDOCARDIAL PRESSURE MEASUREMENT, the entire contents of which are hereby incorporated by reference. Other patents, such as U.S. Pat. No. 5,810,735 to Halperin et al. and U.S. Pat. No. 5,904,708 to Goedeke, which are hereby incorporated by reference, disclose systems for monitoring internal patient parameters such as right ventricular (RV) pressure. Although much of the following description focuses on using pressure measurement catheters to measure endocardial pressure in a human patient, it should be emphasized that this is only one potential application of pressure measurement catheters. As mentioned above, pressure measurement catheters may be used in a wide variety of body vessels, cavities, tissues and the like, and may be used in human patient care, veterinary or research settings.

Implantable devices used for pressure measurement in a human or animal often include a pressure transmission catheter (PTC). A PTC is typically a hollow tubular catheter having a proximal end, a distal end and a lumen. The proximal end is connected to the implantable device and the distal end is positioned in an area of interest for measuring pressure, such as a within a tissue, vessel or body cavity. Typically, a barrier such as a plug or membrane is disposed within the lumen of the PTC near the distal end. Examples of such devices are described in U.S. Pat. Nos. 4,846,191, 6,033,366 and 6,296,615 to Brockway et al., the disclosures of which are hereby incorporated by reference. In such devices, the PTC is typically filled with fluid along most of its length. The barrier is positioned in the catheter lumen to both retain the fluid within the transmission catheter and to contact bodily fluid, such as blood or other substances, in a vessel or other body structure. The barrier is generally configured to be microscopically deflectable, so that pressure changes in the bodily fluid cause the barrier to deflect very slightly. This mechanical deflection of the barrier is transmitted to the fluid in the PTC lumen and the lumen fluid, in turn, transmits the mechanical deflection to a pressure transducer.

Typically, barriers used in PTCs are made of a substance having at least some properties of a gel, so that they are often referred to as "gel plugs", "gel barriers" or "barrier plugs." The material used to make a gel plug is designed to adhere to the inner wall of a PTC lumen to remain in relatively the same position in the lumen during a period of use. One commonly used material for making a gel barrier, for example, is a dimethyl silicone gel.

A manufacturer of an implantable pressure measurement device typically prepares a barrier material and places the material in the lumen of the PTC to form the barrier plug. Often, a protective tip is placed over the end of the catheter to protect the plug during shipping and handling, and the catheter is then provided to a user. At various times, the user may wish to insert additional barrier material into the catheter. For example, occasionally some of the material is inadvertently removed from the end of the catheter when the protective tip is removed, and a user may want to refill the catheter. In a research setting, a user may wish to reuse an implantable pressure measurement device, such as by using the device in multiple animals in succession. Such a user may wish to refill the catheter with barrier material between animals.

One type of barrier material currently used for making barriers in pressure measurement catheters is Dow Q7-2218 gel, made by Dow Corning (Midland, Mich.). Dow Q7-2218 is typically provided as two component parts which must be mixed to form the final gel. Manufacturer's specifications for Dow Q7-2218 suggest mixing the two components in a 1:1 ratio. Such a 1:1 mixture, however, results in a gel that may be appropriate for some applications but is typically not soft enough to allow placement of the gel within a PTC. Therefore, Dow Q7-2218 is typically mixed "off-ratio" to give the gel the desired softness for use in PTCs. In some applications, for example, Dow Q7-2218 is mixed at a ratio of between about 1.65:1 and 1.90:1. Off-ratio mixing, however, has been found to produce a gel that is only slightly cross-linked when made. Such a gel frequently continues to cross link over time, which can be troublesome because the viscosity of the gel increases over time as it continues to cross-link, making placement of the gel in the PTC more difficult and potentially affecting catheter performance. For example, a gel that continues to cross-link may harden within a syringe for injecting the gel into a catheter, typically requiring the use of a power injector rather than a simple handheld syringe. Additionally, such a slightly-cross-linked gel may have a stringy consistency and/or to produce bubbles while hardening into its final form, affecting the performance of the gel barrier.

Although materials such as Dow Q7-2218 gel mixed off-ratio have been used successfully for making barriers in pressure measurement catheter devices, several improvements could be made to such materials. For example, it would be advantageous to have materials which could be made by combining components in a 1:1 ratio while still being sufficiently soft for placement and use in a PTC. Such 1:1 mixing would likely provide several advantages, such as preventing inconsistencies between batches of the material and providing a more stable material. It would also be advantageous to have a fully (or at least substantially) cross-linked barrier material, to enhance stability of the material and reduce "washout" of the material from the catheter during use. (Stability, cross-linking, washout and other terms are described fully below.)

A need exists, therefore, for improved PTC barrier materials that are both (1) sufficiently soft to provide accurate pressure transmission and convenient handling, and (2) fully or substantially cross-linked when made, to provide stability and reduce washout. Ideally, such barrier materials would be convenient to produce and place within a catheter for use. At least some of these objectives will be met by the present invention.

BRIEF SUMMARY OF THE INVENTION

Methods and apparatus of the present invention provide for improved viscoelastic barrier materials for making barriers in devices such as pressure measurement catheters, as well as catheters, kits and methods of making catheters employing such materials. In some embodiments, improved viscoelastic barrier materials are prepared by combining at least one barrier material precursor with an amount of a softener. Although many various softeners may be used, one type of softener is dimethyl silicone oil. In other embodiments, no softener is added and the viscoelastic barrier materials are prepared by combining two components in a 1:1 ratio. Once the viscoelastic barrier material is prepared, it may be placed in a lumen of a pressure transmission catheter (PTC) or similar device. In some embodiments, for example, the material is placed near the distal end of a PTC lumen by injecting the material using a hand syringe. Barrier materials of the present invention have one or more advantageous properties, such as a desired softness, high percentage of cross-linkage, resistance to washout from within a catheter lumen, stability and/or the like.

Generally, viscoelastic barrier materials are configured to optimize several characteristics of the barrier in a PTC. First, barrier materials should be sufficiently soft to allow for relatively easy placement of the materials within a lumen of a PTC and to provide for accurate pressure measurement with minimal hysteresis (delay in pressure change transmission). Softness is sometimes measured as the "penetration value" of a gel made from barrier material precursors. (The viscoelastic barrier materials themselves are typically too soft to measure penetration value.) A barrier material precursor gel that has a high penetration value may typically be used to prepare a relatively soft, viscoelastic barrier material.

Second, the barrier material should be as fully cross-linked as possible when made. Full cross-linking reduces "washout" of the barrier, wherein the barrier material is literally washed out of the lumen of the PTC by blood or other fluid over time. Cross-linking also enhances stability of a barrier, with a stable barrier having a lower change in viscosity over time, compared to a less stable barrier. A stable barrier material also minimizes the amount of fluid that escapes from the fluid-filled PTC due to permeation through, or leakage around, the barrier.

Third, an ideal barrier material will be relatively simple to produce in a consistent manner, so that individual batches of the material are largely similar and complex fabrication techniques are not required. For example, a providing a barrier material may include combining two precursors in a 1:1 ratio in some embodiments. Various embodiments of the present invention include barrier materials having one or more of the above characteristics, as described in further detail below.

In one aspect of the invention, a method of making a pressure measurement catheter includes providing a catheter having a proximal end, a distal end and a lumen, providing a viscoelastic barrier material formed by at least one barrier material precursor combined with an amount of a softener, and placing the barrier gel in the lumen near the distal end of the catheter. In some embodiments, the at least one barrier material precursor is fully cross-linked. This level of cross-linking may be desirable due to improved stability, washout reduction and/or ease of handling, for example. The phrase "fully cross-linked" is defined more fully below in the detailed description but is generally defined as between about 90% and about 100% cross-linked.

In some embodiments, the at least one barrier material precursor comprises a first component combined with a second component in an approximately 1:1 ratio by weight. For example, the first component may be a liquid polymer including a catalyst, and the second component may be a liquid polymer having a cross-linker. In one embodiment, the at least one barrier material precursor, when fully cross-linked, has a penetration range at ten seconds of between about 21 mm and about 37 mm at a temperature of about 25° C. The penetration range in this embodiment and those described below is measured in a container of about 100 g of the barrier material precursor, using a penetrometer having a foot and rod, with the foot having a 1-inch diameter and the foot and rod weighing about 12 g. In another embodiment, the at least one barrier material precursor, when fully cross-linked, has a penetration range at ten seconds of between about 30 mm and about 37 mm at a temperature of about 37° C. These penetration values for the at least one precursor may correlate with barrier materials that have advantageous softness and hysteresis-minimizing properties.

In one embodiment, the softener combined with the at least one precursor is dimehtyl silicone oil. In other embodiments, other softeners may be used, such as but not limited to other silicone oils such as fluorinated silicone oil or phenyl silicone oil, mineral oil, vegetable oil or the like. Similarly, various embodiments call for varying amounts of softener. In one embodiment, for example, softener is combined with the at least one gel component at from 40% to 45% by weight, based on the total weight of the viscoelastic barrier material. In some embodiments, the amount of softener combined with the at least one gel component may be selected to produce a barrier gel having a viscosity of between about 5600 cps and about 7100 cps in an environment having a temperature of about 37° C. In those or other embodiments, the barrier gel may have a viscosity of between about 5200 cps and about 10,100 cps in an environment having a temperature of about 25° C. Various embodiments of the invention may optionally include a barrier material having a viscosity that changes by less than about 500 cps during a period of one year in an environment having a temperature of between about 35° and about 40° C. The barrier material of those or other embodiments may optionally have a viscosity that changes by less than about 1,000 cps during a period of one year in an environment having a temperature of between about 16° and about 25° C. Viscosity measurements in the above ranges may correlate with a relatively stable barrier material that accurately transmits changes in pressure.

In another aspect of the invention, a method of preparing a pressure measurement catheter involves providing a catheter having a proximal end, a distal end and a lumen to a user. A viscoelastic barrier material is also provided to the user so that the user may place the viscoelastic barrier material in the lumen near the distal end of the catheter. The viscoelastic barrier material in this embodiment may have any of the characteristics of the barrier materials described above. The user, such as a physician, may place the barrier material, for example, via a handheld syringe. In some cases, the user may wish to place the material immediately before implanting the catheter in a patient.

In another aspect of the invention, a viscoelastic barrier material for use in a pressure measurement catheter includes at least one barrier material precursor and an amount of a softener combined with the at least one precursor. Again, any of the properties of barrier materials, precursors, softeners and the like described above in relation to the methods of the invention are equally applicable to the viscoelastic barrier materials themselves. For example, the softener may be dimethyl silicone oil, the barrier material precursor may be fully cross-linked and/or the softener may be added in an amount of 40-45% by weight, relative to the viscoelastic barrier material, in various embodiments.

In still another aspect of the invention, a pressure measurement catheter includes a lumen containing a viscoelastic barrier material. The barrier material includes at least one barrier material precursor combined with an amount of a softener, as previously described. Again the viscoelastic barrier material may have any one or more of the characteristics described above.

In another aspect, a pressure measurement catheter includes a lumen containing a fully cross-linked viscoelastic barrier material and the barrier material includes a first component combined with a second component in approximately a 1:1 ratio by weight. The barrier material has a penetration range at ten seconds of between about 21 mm and about 37 mm at a temperature of about 25° C., where the penetration range is measured in a container of about 100 g of the barrier material precursor, using a penetrometer having a foot and rod, the foot having a 1-inch diameter and the foot and rod weighing about 12 g. In some embodiments, the barrier material also has a penetration range at ten seconds of between about 30 mm and about 37 mm at a temperature of about 37° C. Also in some embodiments, the first component comprises a liquid polymer including a catalyst, and the second component comprises a liquid polymer having a cross-linker.

Finally, in another aspect, a kit of the present invention includes a pressure measurement device including a catheter having a proximal end, a distal end and a lumen, a viscoelastic barrier material disposed within the lumen to form a barrier and instructions for use. The barrier material comprises at least one barrier material precursor and an amount of softener combined with the precursor. Alternatively, another kit of the invention comprises a syringe, an amount of viscoelastic barrier material and instructions for using the syringe to place the viscoelastic barrier material into a lumen of a pressure measurement catheter. In one embodiment, the viscoelastic barrier material is disposed within the syringe.

Various embodiments of the present invention are further described in the drawing figures and detailed description below.

BRIEF DESCRIPTION OF THE DRAWINGS

FIGS. 1D-1O illustrate longitudinal sectional views of various pressure transmission catheters, according to various embodiments of the invention.

DETAILED DESCRIPTION OF THE INVENTION

Methods of the present invention generally include providing a viscoelastic barrier material, providing a pressure measurement catheter (or pressure transmission catheter (PTC)), and placing the viscoelastic material in a lumen of the PTC to form a barrier. In some embodiments, the viscoelastic material is prepared by combining at least one barrier material precursor with an amount of a softener. In other embodiments, the material is prepared by combining two precursor components in a 1:1 ratio to produce a fully cross-linked material.

Devices of the invention include viscoelastic barrier materials for use in PTCs and other pressure measurement devices, as well as various pressure measurement devices including viscoelastic barriers. Viscoelastic barrier materials of the present invention have one or more improved characteristics for use in forming PTC barriers. For example, many embodiments of barrier materials have sufficient softness to allow for easy handling and placement and to enhance pressure transmission and reduce hysteresis. Some embodiments of barrier materials are fully cross-linked, nearly fully cross-linked or at least sufficiently cross-linked to provide enhanced stability and decreased washout. These and other characteristics of viscoelastic barrier materials are described more fully below. The following description illustrates exemplary embodiments of barrier materials, pressure measurement catheters and methods for making and using such materials and catheters. The description of these embodiments is provided for illustrative purposes only and should not be interpreted to limit the scope of the invention as set forth in the claims.

Figure 1:
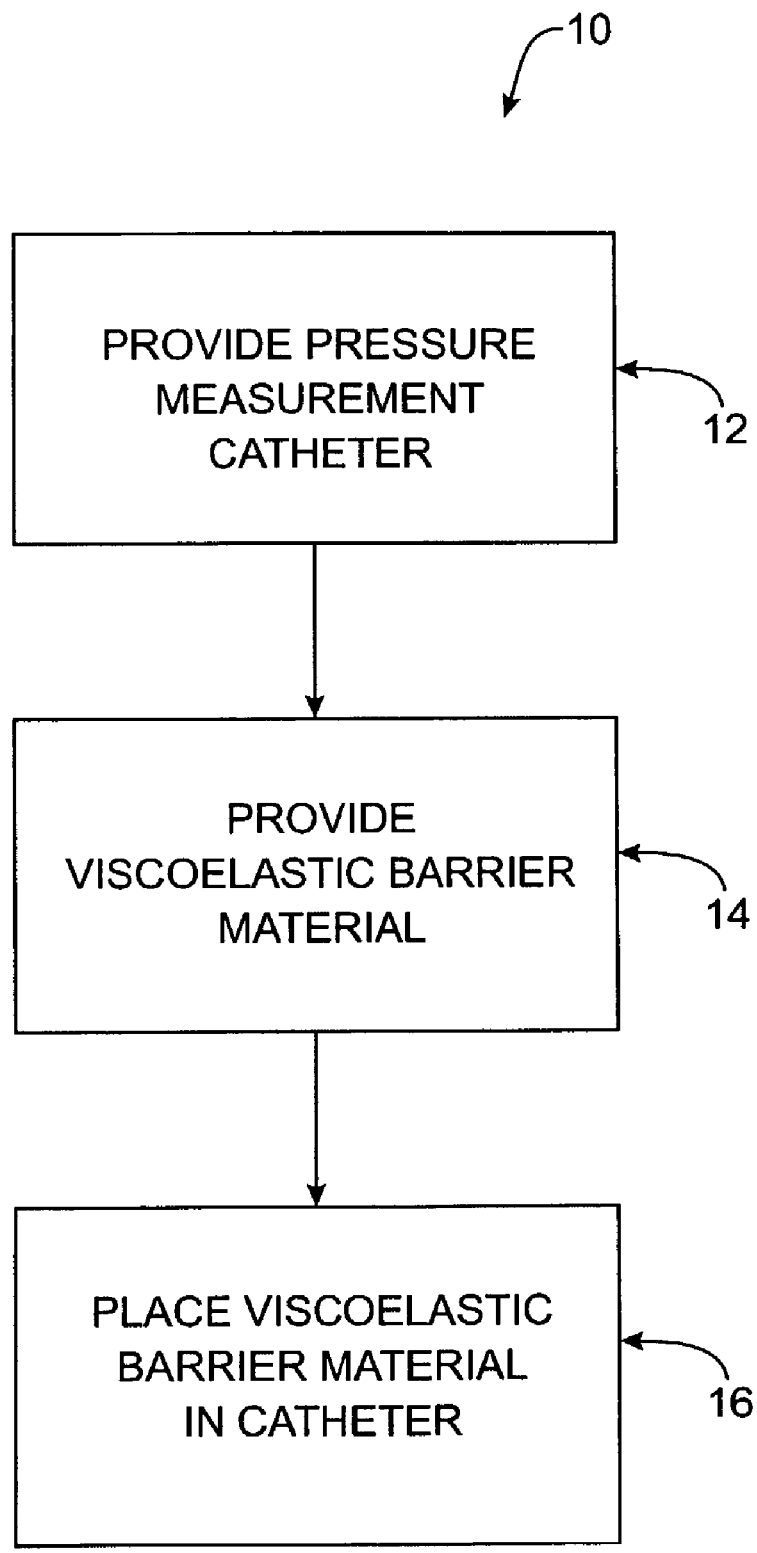
FIG. 1 is a block diagram of a method for making a pressure measurement catheter having a viscoelastic barrier material according to an embodiment of the present invention.

With reference to FIG. 1, a method 10 for making a pressure measurement catheter having an improved barrier suitably includes providing a pressure measurement catheter 12 having a proximal end, a distal end and a lumen. The method also involves providing a viscoelastic barrier material 14 formed by combining at least one barrier material precursor with an amount of a softener. The viscoelastic barrier material is then placed into the lumen of the catheter 16, typically near the distal end. Although these steps are often carried out by a manufacturer of a pressure measurement catheter, in some embodiments the viscoelastic barrier material and the catheter may be provided to a user in a form to allow the user to place the barrier material into the catheter. For example, the user might place the barrier material in the catheter immediately or almost immediately before placing the pressure measurement device in a patient for use. Various methods of the present invention are described further below.

Barriers of the present invention may be used in any suitable catheter or implantable device. In one embodiment, barrier materials are used in a PTC that is part of an implantable pressure measurement device for measuring endocardial pressure in a human patient. Examples of such pressure measurement devices are described in U.S. patent application Ser. No. 10/077,566, previously incorporated by reference, and in U.S. Pat. Nos. 4,846,191, 6,033,366 and 6,296,615 to Brockway et al., the disclosures of which were previously incorporated herein by reference. In other embodiments, for example as described in detail in U.S. Pat. No. 4,846,191, pressure transmission catheters may be used in animal research, such as for measuring endocardial, arterial, venous, cerebral, intraocular, urinary, intrauterine, penile, thoracic cavity and/or various other vascular or tissue pressures, or for conducting in vitro testing. Thus, although much of the following description focuses on using pressure measurement catheters to assess endocardial pressure in humans, it should be emphasized that the embodiments described, or variations of those embodiments, may be used in many other clinical and/or research settings.

The description below starts by providing details on exemplary pressure measurement catheter devices and then continues by describing exemplary viscoelastic barriers, barrier materials and methods for making and using such barrier materials and catheters, according to various embodiments of the present invention.

Exemplary Pressure Measurement Catheter Apparatus and Systems

In one embodiment, a pressure measurement system may include an implantable telemetry device (ITD) 20, as shown in FIGS. 1-2 and described further below, and one or more data collection systems. For example, the system may include a home (i.e., local) data collection system (HDCS), which receives the telemetry signal, optionally corrects for fluctuations in ambient barometric pressure, evaluates the validity of the received signal, and, if the received signal is deemed to be valid, extracts parameters from that signal and stores the data according to a physician-defined protocol. The system may also include a physician (i.e., remote) data collection system (PDCS), which receives the data signal from the HDCS via a telecommunication system (e.g., the Internet). The PDCS receives the data signal, evaluates the validity of the received signal and, if the received signal is deemed to be valid, displays the data, and stores the data according to a physician-defined protocol. With this information, the system enables a treating physician to monitor endocardial pressure in order to select and/or modify therapies for a patient to better treat diseases such as CHF and its underlying causes.

For example, a pressure measurement system may be used for assessment of pressure changes (e.g., systolic, diastolic, and LV max dP/dt) in the main cardiac pumping chamber (the left ventricle (LV)). These pressures are known to fluctuate with clinical status in CHF patients, and they provide key indicators for adjusting treatment regimens. For example, increases in end-diastolic pressure, changes in the characteristics of pressure within the diastolic portion of the pressure waveform, and decreases in maximum dP/dt, or increases in minimum dP/dt together suggest a deteriorating cardiac status. As used herein, LV max dP/dt refers to the maximum rate of pressure development in the left ventricle. These measurements could be obtained either during clinic visits or from the patient at home, from the proposed device and stored for physician review. The physician can then promptly adjust treatment. In addition, the system may assist in management of patients when newer forms of device therapy (e.g., multiple-site pacing, ventricular assist as a bridge to recovery, or implantable drugs pumps) are being considered. Again, for more detailed description of an exemplary pressure measurement system, refer to U.S. patent application Ser. No. 10/077,566, previously incorporated by reference.

Figure 1A:
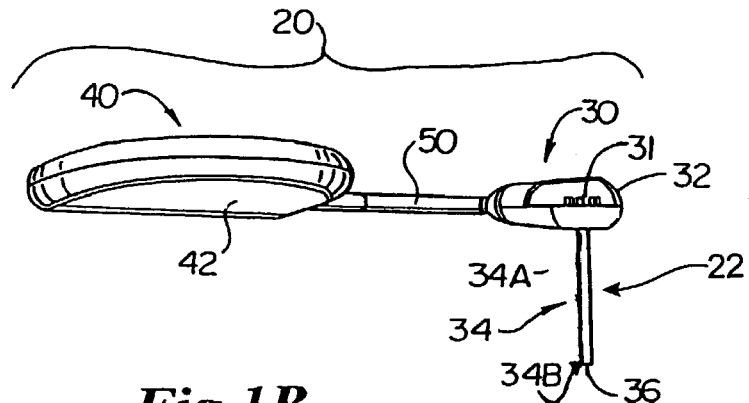
FIG. 1A is a side view of an implantable pressure measurement telemetry device, including a remote sensor assembly and telemetry unit, according to an embodiment of the invention.
Figure 1B:
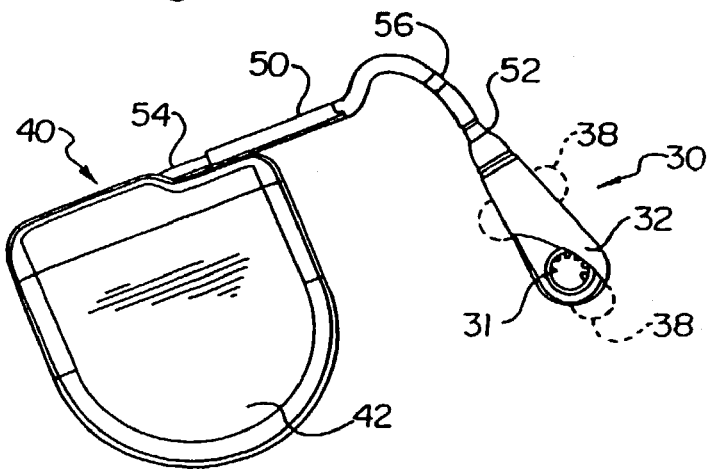
FIG. 1B is a top view of the implantable pressure measurement device illustrated in FIG. 1A.
Figure 1C:
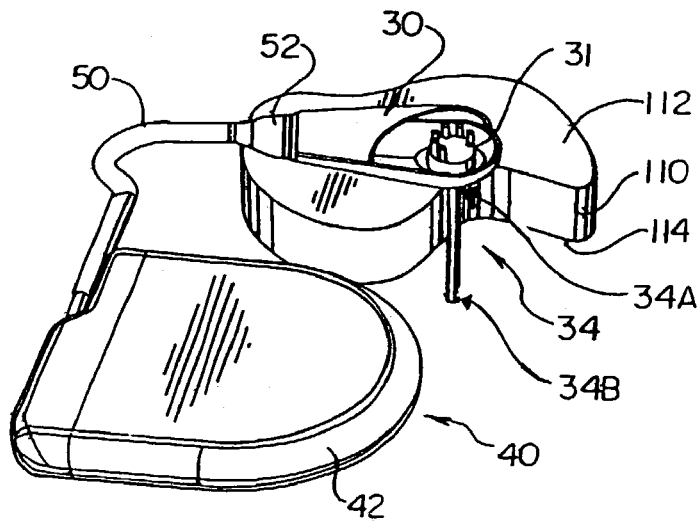
FIG. 1C is a perspective view of the implantable pressure measurement device illustrated in FIG. 1A, showing the pressure transmission catheter of the remote sensor assembly extending across a heart wall.
Figure 10:
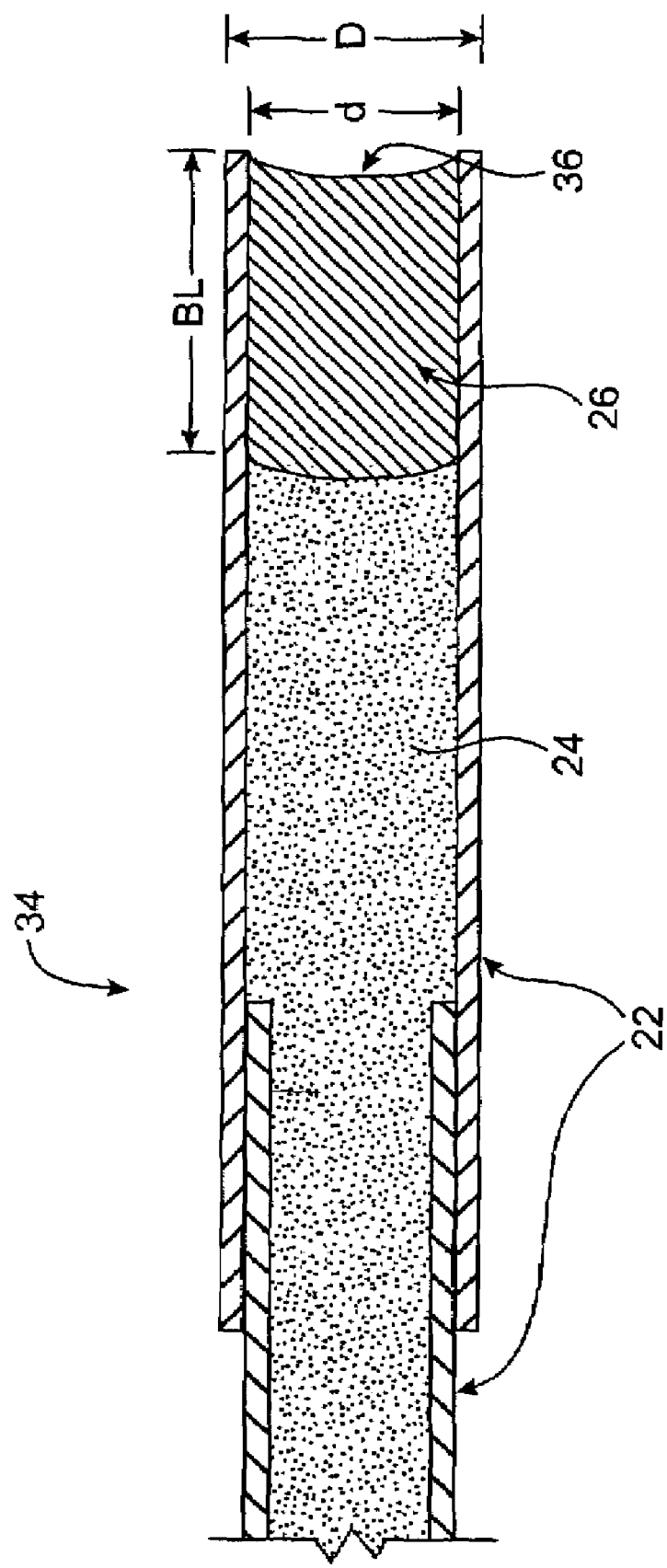

With reference now to FIGS. 1A-1C, an implantable telemetry device (ITD) 20 may include a remote sensor assembly (RSA) 30 for measuring a pressure, connected via a lead 50 to a telemetry unit (TU) 40 for telemetering measured pressure data to a receiver located outside the body. Telemetry device 20 may be used, for example, for measuring endocardial blood pressure in the LV. An alternative construction mounts all of the ITD 20 in a single housing which may be implanted in any of the positions of the RSA 30 described hereinafter, or directly in a heart chamber. For examples of alternative embodiments of the RSA 30 and TU 40, reference may also be made to U.S. Pat. No. 4,846,191 to Brockway et al., which describes various embodiments for use in animal research. Other embodiments are described in U.S. Pat. No. 6,033,366 to Brockway et al., U.S. Pat. No. 6,296,615 to Brockway et al., and PCT Publication WO 00/16686 to Brockway et al., the disclosures of which have previously or are hereby incorporated herein by reference.

The RSA 30 includes a pressure transducer 31 and an electronics module (not shown) contained within housing 32. The sensor housing 32 protects the pressure transducer 31 and the electronics module from the harsh environment of the human body. The housing 32 may be fabricated of a suitable biocompatible material such as titanium and may be hermetically sealed. The outer surface of the housing 32 may serve as an electrogram (EGM) sensing electrode. The proximal end of the housing 32 includes an electrical feed-through to facilitate connection of the electronics module in the housing 32 to a flexible lead 50. The distal bottom side of the housing includes a pressure transducer header to facilitate mounting of the pressure transducer 31 and to facilitate connection to a pressure transmission catheter (PTC) 34. The top side of the housing 32 may have a visible marking directly opposite the location of the PTC 34 on the bottom side such that the location of the PTC 34 can be visualized during surgery.

The housing 32 may include one or more connection means 38 such as suture rings (shown in phantom), tines, helical anchors and/or the like, to facilitate connection to tissue at the implant site (e.g., epicardium). As an alternative, the connection means 38 may comprise a mesh fabric (not shown) disposed over the housing 32 or integrally formed/connected to the bottom surface of the housing 32. Such a mesh fabric may be attached to the epicardial surface by adhesive, sutures, or other suitable means conventional in the surgical art. Enhanced long term attachment to the epicardial surface is enhanced by fibrosis which is encouraged by the rough texture of the mesh fabric. The mesh fabric may comprise a biodegradable or biodegradable/non-biodegradable material composite, and the outside (parietal) surface may be made smooth to minimize in-growth adhesion to the surrounding tissues (e.g., rib cage). Preferably, the mesh fabric may have a partially open weave and/or be formed of a transparent or semi-transparent material to increase visibility through the mesh fabric, reducing the likelihood of attachment to essential cardiac features.

The pressure transducer 31 and the electronics module, both disposed in housing 32, may be the same or similar to those described in U.S. Pat. Nos. 4,846,191, 6,033,366, 6,296,615 or PCT Publication WO 00/16686, all to Brockway et al. The electronics module provides excitation to the pressure transducer 31, amplifies the pressure and EGM signals, and may digitally code the pressure and EGM information for communication to the telemetry unit 40 via the flexible connecting lead 50. The electronics module may also provide for temperature compensation of the pressure transducer 31 and provide a calibrated pressure signal. Although not specifically shown, it may be useful to include a temperature measurement device within the electronics module to compensate the pressure signal from temperature variations. For example, the temperature measurement may select a look up table value to modify the pressure reading. This operation may be performed in any of the RSA 30, TU 40, or HDCS.

The PTC 34 refers pressure from the pressure measurement site (e.g., LV) to the pressure transducer 31 located inside the sensor housing 32. Exemplary PTCs 34 are described in further detail below, but various embodiments generally include a catheter body 22 having a proximal end 34A and a distal end 34B and at least one opening or aperture 36 disposed at or near the distal eng 34B. The PTC 34 may optionally include one or more EGM electrodes or other physiological sensors as described in U.S. Pat. No. 6,296,615 to Brockway et al.

The proximal end 34A of the PTC 34 is connected to the pressure transducer 31 via a nipple tube (not shown), thus establishing a fluid path from the pressure transducer 31 to the distal end 34B of the PTC 34. The proximal end 34A may include an interlocking feature to secure the PTC 34 to the nipple tube of the pressure transducer 31. For example, the nipple tube may have a knurled surface, raised rings or grooves, etc., and the proximal end 34A may include an outer clamp, a silicone band, a spring coil or a shape memory metal (e.g., shape memory NiTi) ring to provide compression onto the nipple tube.

Referring now to FIGS. 1D-1N, a PTC 34 may have any of a number of suitable configurations. Generally, each PTC 34 includes a catheter body 22 defining a lumen 24 and having at least one aperture 36 at or near the distal end of the PTC 34. One or more barriers 36 are disposed within the lumen 24 and/or the catheter body 22 and a fluid is contained within the lumen 24 by the barrier 36.

The barrier 26 is generally configured and disposed in the lumen 24 to isolate the liquid-filled portion of the lumen 24 of the PTC 34 from bodily fluids, without impeding pressure transmission therethrough. Barriers 26, barrier materials, methods and the like are described in further detail below, but generally the barrier 26 comprises one to several millimeters of a viscoelastic barrier material positioned within the lumen 24 of the PTC 34 near the opening 36 at the distal end of the PTC 34. The barrier 26 comes into contact with blood (or other bodily fluids or substances in other settings) and transfers pressure changes in the blood, allowing changes in blood pressure to be transmitted through the fluid-filled lumen 24 of the PTC 34 and measured by the pressure transducer 31. The barrier 26 is confined in the lumen 24 by the cohesive and adhesive properties of the barrier material and the interface with catheter materials. The chemistry of the barrier 26 is chosen to minimize the escape of the fluid in the remainder of the PTC 34 by permeating through, or leaking around, the barrier 26.

Again, barriers 26, barrier materials and methods for making and using barriers 26 are discussed in further detail below. Generally, however, in one embodiment the fluid in the lumen 24 comprises fluorinated silicone oil and the barrier 26 comprises a dimethyl silicone barrier material precursor combined with an amount of dimethyl silicone oil. Other embodiments may include a fluorinated silicone barrier material precursor and fluorinated silicone oil, a phenyl silicone barrier material precursor and phenyl silicone oil, or any other suitable precursor/oil combination. Preferably, in order to place viscoelastic barrier material into the lumen 24 to form the barrier 26, as well as to obtain accurate measurements, a viscoelastic barrier precursor used to form the barrier 26 is relatively soft, as measured by a relatively high penetration value for the precursor. Also preferably, the barrier 26 may be sufficiently soft so as to not induce hysteresis, but not so soft that significant washout occurs. Washout is typically reduced by choosing a barrier material that becomes fully cross-linked and has a low solubility fraction. The use of a fully cross-linked barrier material also reduces or eliminates permeation of the transmission fluid in lumen 24 through the barrier 26. These and other characteristics of barriers 26 are described in further detail below, after the general description of the ITD 20.

In some embodiments, as shown in FIGS. 1E and 1N, the barrier 26 is configured to be recessed from the aperture 36 or extreme distal end of the PTC 34, to shelter the barrier 26 from physical contact and subsequent disruption that may occur during shipping and handling of the device 20 or during insertion of the device 20 into the heart. For example, in some embodiments the barrier 26 may be recessed by between about 0.1 mm and about 5.0 mm, preferably by between about 0.1 mm and about 1.0 mm and even more preferably about 0.5 mm. In other embodiments, the barrier 26 may be recessed by more than 5.0 mm, depending on the size of the PTC 34. A recessed barrier 26 may be achieved by stem compression during placement of the viscoelastic barrier material in the catheter to reduce lumen volume during filling or by thermally induced techniques. Alternatively, as shown in FIG. 1D, the barrier 26 may be made flush with the distal end of the PTC 34, for example by utilizing an automated guillotine to sever the barrier 26 distal to the tip. The distal tip of the PTC 34 and the barrier 26 contained near the opening 36 may be protected by other means, such as by the use of a tip protector such as a twist-on/off cap that mechanically interlocks on the proximal portion of the PTC 34, providing protection of the tip and barrier 26 via an annular clearance. The tip protector may, in another embodiment, have a side release mechanism similar to a binder clip that again provides annular clearance at the tip but allows radial removal of the protector rather than axial removal. This annular clearance zone is more likely to be maintained during removal with the side clip approach. Either approach results in a cover which may be removed prior to insertion. Protection of the distal tip may also be achieved by utilizing a pocket defined in the final packaging that has sufficient clearance such that contact with the distal tip of the PTC 34 is avoided.

The pressure transmission fluid contained within the lumen 24 of the PTC 34 proximal of the barrier 26 may be any suitable fluid, typically of relatively low viscosity, and may be used to tune the frequency response of the PTC 34 by adjusting the viscosity of the transmission fluid. Preferably, the pressure transmission fluid comprises a relatively stable and heavy molecular weight fluid. Also preferably, the specific gravity of the transmission fluid is relatively low in order to minimize the effects of fluid head pressure that could result as the orientation of the PTC 34 changes relative to the sensor 31. The pressure transmission fluid preferably has minimal biological activity (in case of catheter or barrier failure), has a low thermal coefficient of expansion, is insoluble in the barrier 26, has a low specific gravity, has a low volatility, has a negligible rate of migration through the walls of PTC 34, and has a low viscosity at body temperature. In one embodiment, the pressure transmission fluid may incorporate end-group modifications (such as found in flourinated silicone oil) to make the transmission fluid impermeable in the material used to make the barrier 26. In another embodiment the fluid comprises a perfluorocarbon.

The one or more apertures 36 of the PTC 34 may be positioned at any desired location(s) along the catheter body 22. For example, in the embodiments shown in FIGS. 1A-1E and 1L-1N, the aperture 36 is located at the extreme distal end of the catheter body 22. Alternatively, an aperture 36 may be located in a side wall of the catheter body 22 as shown in FIGS. 1F-1K. In FIG. 1F, the PTC 34 includes a lateral facing aperture 36 filled with barrier material 26. In FIG. 1G, two lateral apertures 36 are provided, and in FIG. 1H, a single lateral aperture 36 in combination with a distal facing aperture 36 is provided on the PTC 34.

In some embodiments, the aperture 36 has the same cross-sectional area as the lumen 24, as shown in FIGS. 1C-1M. In other embodiments, as in FIGS. 1D and 1N, the aperture 36 has a larger surface area than the lumen 24 of the PTC 34. This may be achieved, for example, by giving catheter body 22 a flared or widened distal portion, again as shown in FIGS. 1D and 1N. A widened aperture 36, relative to the rest of catheter body 22, reduces movement of the barrier 26 during events that change either the volume of the transmission fluid or the internal volume of lumen 24, such as occurs during thermal expansion and contraction, bending, and hydration of the catheter material of PTC 34. Reducing the degree of displacement of the barrier 26 during bending of PTC 34 has the effect of reducing measurement artifact that occurs during normal movement of the subject into which the RSA 30 is implanted. Reducing the degree of displacement of the barrier 26 during bending of PTC 34 reduces the maximum amount of dead space (space defined by recessed barrier 26 as seen in FIG. 1E) within the PTC 34 and beyond the barrier 26, and therefore, contributes to improved patency in blood. Moreover, the larger surface area of the opening(s) 36 also may increase the frequency response of the device.

As seen in FIG. 1D, proximal and distal portions of the PTC 34 may be flared to have a larger inside diameter (ID) and outside diameter (OD), for different purposes. The distal end of the PTC 34 may be flared to provide an aperture 36 having a larger surface area as discussed above, and a proximal portion of the PTC 34 may be flared to accommodate the nipple tube (not shown) and provide a compression fit thereon. The proximal flared portion may have an ID that is smaller than the nipple tube to provide a compression fit that will be stable for the life of the RSA 30. In one embodiment, for example, the proximal flared portion may have an ID of 0.026 inches, an OD of 0.055 inches, and a length of about 7 mm. The stem (mid) portion may have an ID of 0.015 inches, and OD of 0.045 inches, and a length of about 7 mm. The distal flared portion may have an ID of 0.035 inches, an OD of 0.055 inches, and a length of about 4 to 5 mm. The proximal taper may have a length of about 0.5 mm and the distal taper may have a length of about 1.25 mm. Many other combinations of dimensions are suitable and contemplated within the scope of the invention.

With reference now to FIG. 1O, for example, alternative dimensions for several embodiments of PTC 34 may be described. For example, one embodiment of a PTC 34 for use in a mouse may have an outer diameter (D) of about 0.016 in., an inner diameter (d) of about 0.012 in. and a barrier length (BL) of about 0.079 in. Another embodiment, for use in small animals, may have an outer diameter of about 0.030 in., an inner diameter of about 0.021 in. and a barrier length of about 0.12 in. In yet another embodiment, for use in large animals, the PTC 34 may have an other diameter of about 0.055 in., an inner diameter of about 0.045 in. and a barrier length of about 0.26 in. Of course, many other suitable dimensions and combinations are possible.

In various embodiments, the size and position of the barrier 26 may vary as desired. As previously described, for example, the barrier 26 may be positioned in the lumen 24 so as to be recessed from the aperture 36. In some embodiments, for example, the barrier 26 may be recessed by between about 0.1 in. and about 1.0 in. Additionally, the barrier 26 itself may have any suitable length. For example, in some embodiments the barrier 26 will be about 2.5 in. to about 3.0 in. long. In cases where a relatively short PTC 34 is utilized, the lumen 24 may be almost completely filled with the barrier 26. Such lengths and positions may vary with changes in temperature and many other combinations of barrier size, shape, position within the lumen 24 and/or the like are contemplated within the scope of the invention.

In some embodiments, a thin membrane 28 may be disposed over one or more apertures 36. For example, as shown in FIG. 1K, a thin membrane material 28 is disposed over the lateral apertures 36. As shown in FIG. 1L, a thin membrane material 28 is disposed over the distal facing aperture 36. The thin membrane material 28 may comprise a thin, biocompatible polymeric material.

Figure 2A:
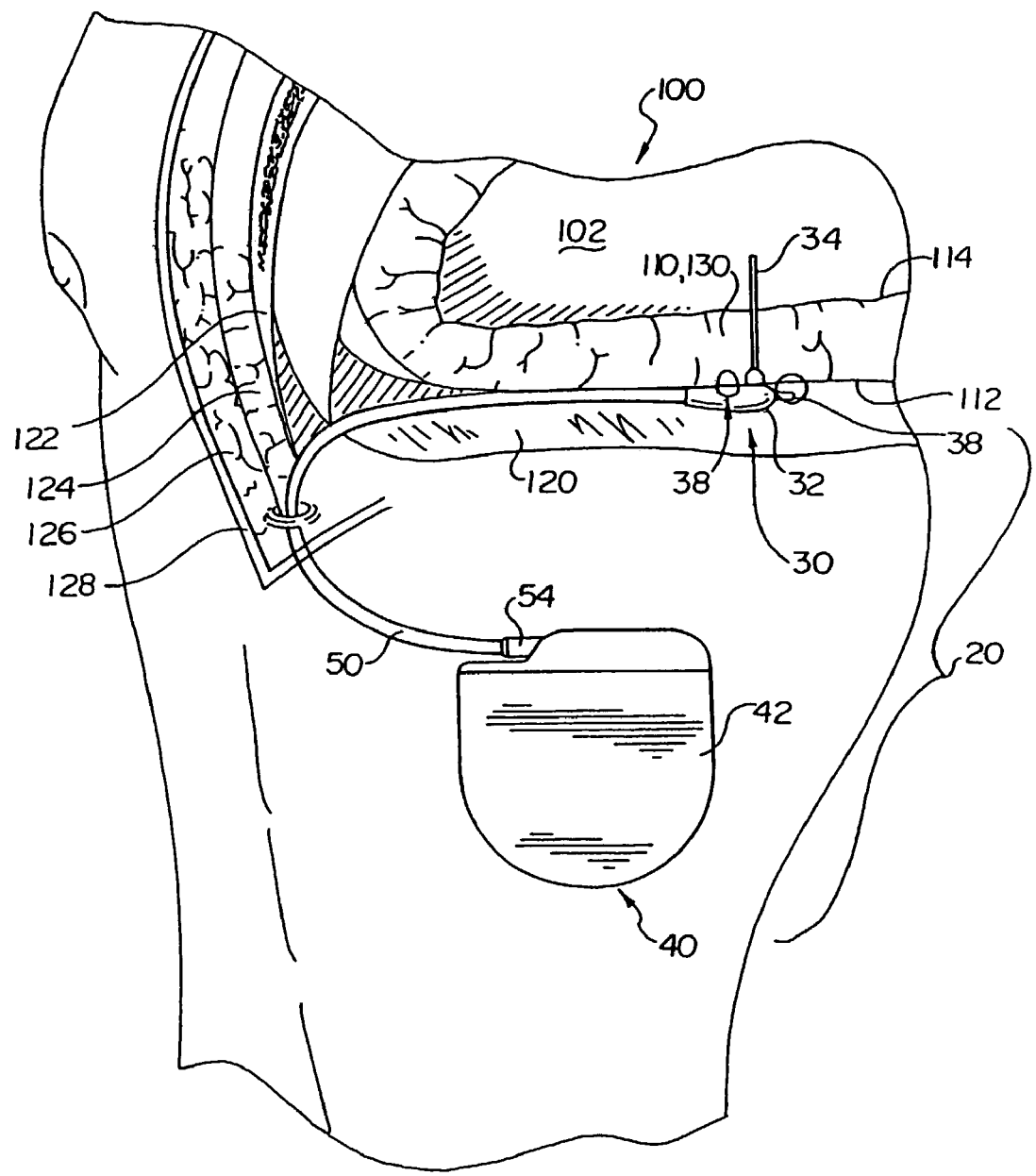
FIG. 2A illustrates a remote sensor assembly and telemetry unit implanted in a patient, with pressure transmission catheter positioned across the left ventricular heart wall, according to an embodiment of the invention.
Figure 2B:
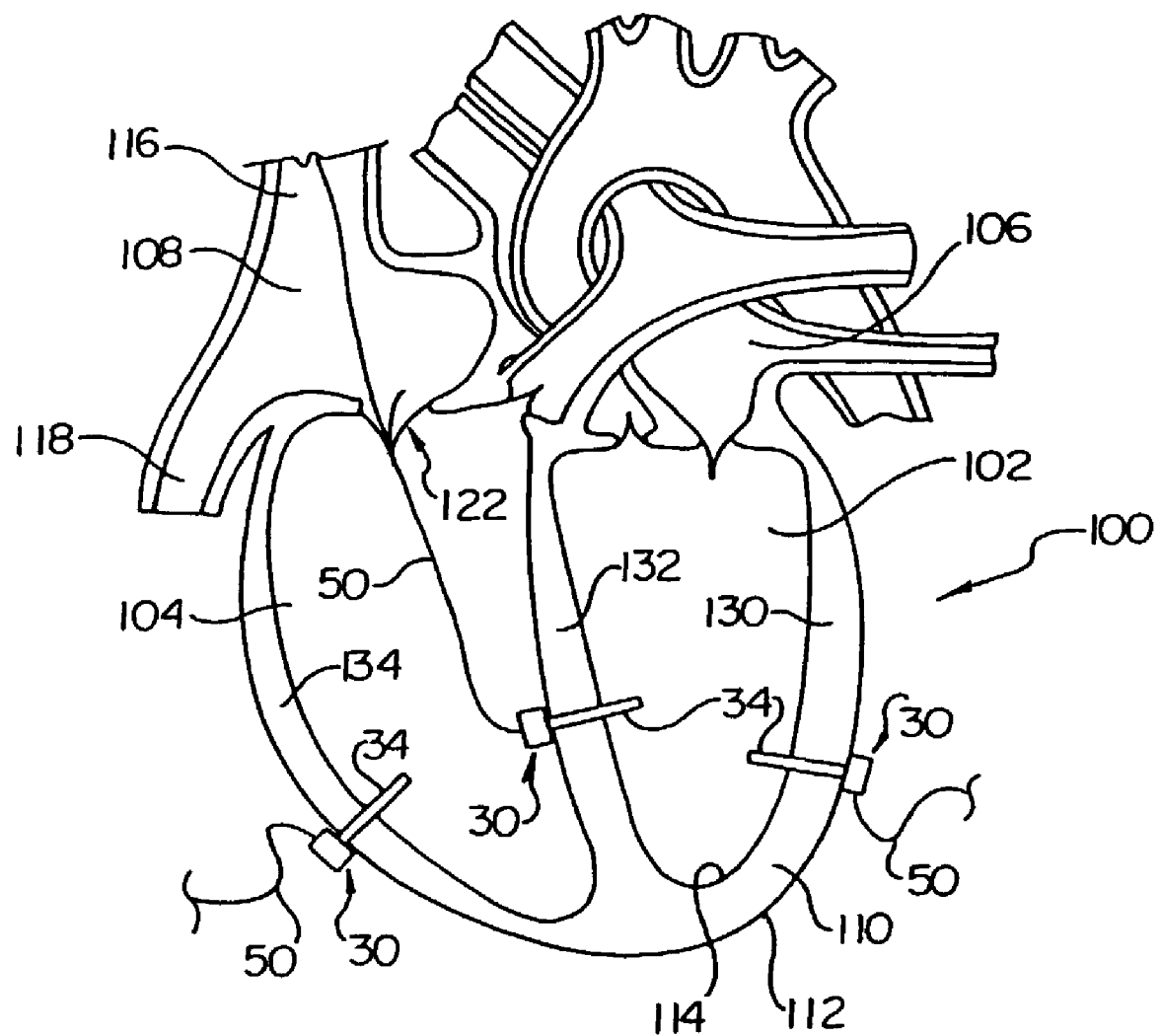
FIG. 2B schematically illustrates various possible anatomical implant positions for the remote sensor assembly, according to various embodiments of the invention.

Generally, the PTC 34 may have any suitable length. In some embodiments, as shown in FIGS. 2A and 2B, the PTC 34 has a length sufficient to extend across a myocardial wall and into a heart chamber. In such embodiments, for example, the catheter body 22 may have a length of about 12 mm to about 30 mm. The PTC 34 preferably has a length that provides adequate access across the myocardium and into the left ventricle while being as short as possible to minimize head height effects associated with the fluid-filled lumen 24. Other embodiments for implantation in a human heart or in any other location may have any suitable length. The PTC 34 may be straight or curved, depending on the particular orientation of the RSA 30 relative to the heart wall and the chamber defined therein at the insertion point.

In some embodiments, an antithrombogenic coating may be applied to a distal portion of the catheter body 22 that is positioned within a left ventricle or other structure, and a proximal portion disposed within a heart wall or similar structure may be over-molded with silicone to provide stress relief, flex fatigue strength, and a compliance matching mechanism at the entrance to the myocardium. Because the heart walls are dynamic structures subject to expansion and contraction, a proximal portion may be made relatively crush-resistant, with sufficient crush resistance to prevent collapse caused by myocardial contraction. A distal portion may be made relatively flexible with radiused corners to provide an atraumatic tip.

For example, as seen in FIG. 1M, the PTC 34 may comprise a stainless steel or titanium hypotube 22B (e.g., an extension of the nipple tube) extending through a proximal portion, with a polymeric tube 22A extending over and beyond the hypotube 22B into a distal portion 34B. Alternatively, the proximal portion may be formed of a polymeric material having a relatively high durometer and the distal portion may be formed of a polymeric material having a relatively low durometer.

Generally, any suitable material may be used to form the PTC 34. For example, some PTCs 34 are made from TECOFLEX™ (available from Thermedics Polymer Products), CHRONOFLEX™ (available from the CT biomaterials Division of Cardiotech Inernational Inc.), PELLETHANE™ (available from Dow Plastics of The Dow Chemical Company) or BIONATE™ (available from The Polymer Technology Group, www.polymertech.com). In other embodiments, additional or alternative materials may be used. In various embodiments, catheter body 22 may include proximal and distal portions formed of separate tubes connected together, or may comprise a single tube with a gradient stiffness, such as provided by interrupted layer coextrusion processes. As a further alternative, a proximal portion and a distal portion may comprise a polymeric tube having a relatively low durometer, with a rigid polymeric sleeve having a relatively high durometer extending over the proximal portion.

Referring now to FIG. 2A, the ITD 30 is shown surgically implanted in/on a heart 100 of a patient. In this exemplary embodiment, the present invention provides for insertion of the PTC 30 directly into the LV 102 across the wall 130 (i.e., myocardium 110) 110 of the heart 100 for the purpose of measuring LV pressure. This allows for chronic monitoring of pressure in the LV chamber 102 of the heart 100.

Implantation of the ITD 20, including RSA 30 and TU 40, may take place during an open chest procedure such as would normally be done to perform coronary artery bypass or valve repair/replacement. Alternatively, the ITD 20 may be implanted in a separate surgical procedure. In such a case, the surgeon performs a median sternotomy, cutting across the dermal layer 128, sub-dermal tissue 126, muscle layer 124, and sternum 122. The surgeon then cuts the pericardial sac 120 to expose the heart 10, down to the LV apex.

The PTC 34 is introduced into the LV 102 at the inferior apical segment using a split-sheath introducer (not shown). The split-sheath introducer facilitates insertion of the PTC 34 into the myocardium 110 and protects the PTC 34 from damage that may otherwise occur during the insertion process. Following insertion of the PTC 34, the split-sheath introducer is removed and discarded.

The split-sheath introducer may incorporate handles that extend outward beyond the periphery of the RSA 30 for easy access. The handles may be relatively long with raised ears of softer durometer to facilitate easy griping. A solid core needle (trocar) may also be used to eliminate coring and emboli formation which may be associated with hollow needles and to maximize compression exerted on the PTC 34 by the myocardium, thereby accelerating hemostasis. Radiopaque materials may be incorporated into the PTC 34, the split sheath introducer (not shown), and/or the trocar to insure trackability via x-ray fluoroscopy.

The PTC 34 is automatically positioned within the LV 102, in terms of depth, by virtue of its length when the housing 32 of the RSA 30 contacts the myocardial surface. In other embodiments wherein the length of the PTC 34 and the housing 32 do not limit depth penetration, the PTC 34 may be positioned within the LV chamber 102 by pulling the PTC 34 back until the pressure signal disappears, and then advancing the PTC 34 approximately 2-10 mm to assure that the tip is not in the immediate proximity of trabeculae (not shown). Inserting the PTC 34 as such reduces the likelihood that fibrous tissue will overgrow the tip of the PTC 34. The entry point of the PTC into the epicardium 112 may be secured for hemostasis by fine purse string suture. The purse string sutures may extend through the epicardium and into the myocardium. The sensor housing 32 may then be anchored to the pericardium with a fine suture material utilizing the suture ports 38 integrated into the sensor housing 32. The sensor housing 32 and PTC 34 are positioned in a manner that provides sufficient slack in the portion of the PTC 34 external to the myocardium 110 in order to absorb stress. Again, these steps are useful with embodiments wherein the length of the PTC 34 and the housing 32 do not limit depth penetration into the LV chamber 102. The embodiment illustrated in FIG. 2A does not require these particular steps for correctly positioning the PTC 34 in the LV chamber 102.

In the embodiment illustrated in FIG. 2A, the proximal lead 50 is then draped over the open pericardial edge, and brought caudally inferior laterally under the abdominal fascia. A 4-5 cm horizontal incision is made on the left upper quadrant of the abdominal wall and a subcutaneous pocket is created. The proximal end of the flexible lead 50 may be brought into the subcutaneous pocket through an introducer placed through the abdominal fascia. If a releasable connection 54 is utilized, the lead 50 is attached to the TU 40, tested using a PDCS, and the TU 40 is placed in the subcutaneous pocket. The pocket and the chest are then closed.

The flexible lead 50 connects the electronics module 33 and sensor housing 32 to the telemetry unit 40. The lead 50 may contain, for example, four conductors—one each for power, ground, control in, and data out. The lead 50 may incorporate conventional lead design aspects as used in the field of pacing and implantable defibrillator leads. The lead 50 may include a strain relief 52 at the connection to the proximal end of the sensor housing 32. The lead 50 may also include a connector 54 which allows the RSA 30 to be connected and disconnected from the TU 40 in the surgical suite to facilitate ease of implantation, at a later time should it be necessary to change the TU 40, or for any other circumstance. The lead 50 may optionally include one or more EGM electrodes 56. When EGM electrodes are carried along the lead, the number of conductors will need to be modified to suit the design.

The TU 40 includes telemetry electronics (not shown) contained within housing 42. The TU housing 42 protects the telemetry electronics from the harsh environment of the human body. The housing 42 may be fabricated of a suitable biocompatible material such as titanium or ceramic and is hermetically sealed. The outer surface of the housing 42 may serve as an EGM sensing electrode. If a non-conductive material such as ceramic is used for the housing 42, conductive electrodes may be attached to the surface thereof to serve as EGM sensing electrodes. The housing 42 is coupled to the lead 50 via connector 54, and includes an electrical feed-through to facilitate connection of the telemetry electronics to the connector 54. The telemetry electronics (not visible) disposed in the TU 40 may be the same or similar to those described in U.S. Pat. Nos. 4,846,191, 6,033,366, 6,296,615 or PCT Publication WO 00/16686, all to Brockway et al.

Referring now to FIG. 2B, various possible anatomical implant positions for the RSA 30 are illustrated. To facilitate a discussion of the various possible anatomical implant positions, the heart 100 is shown schematically. The heart 100 includes four chambers, including the left ventricle (LV) 102, the right ventricle (RV) 104, the left atrium (LA) 106, and the right atrium (RA) 108. The LV 102 is defined in part by LV wall 130, RV 104 is defined in part by RV wall 134, and the LV 102 and the RV 104 are separated by septal wall 132.

The right atrium 108 receives oxygen deprived blood returning from the venous vasculature through the superior vena cava 116 and inferior vena cava 118. The right atrium 108 pumps blood into the right ventricle 104 through tricuspid valve 122. The right ventricle 104 pumps blood through the pulmonary valve and into the pulmonary artery which carries the blood to the lungs. After receiving oxygen in the lungs, the blood is returned to the left atrium 106 through the pulmonary veins. The left atrium 106 pumps oxygenated blood through the mitral valve and into the left ventricle 102. The oxygenated blood in the left ventricle 102 is then pumped through the aortic valve, into the aorta, and throughout the body via the arterial vasculature.

By way of example, not limitation, the RSA 30 may be implanted such that the distal end of the PTC 34 resides in the LV 102, the RV 104, or any other chamber of the heart 100, although the LV 102 is preferred for the reasons set forth previously. For example, the PTC 34 may be positioned across the LV wall 130 such that the distal end of the PTC 34 is disposed in the LV 102 as described with reference to FIG. 2A. Alternatively, the PTC 34 may be positioned across the RV wall 134 such that the distal end of the PTC 34 is disposed in the RV 104 in a similar manner as that described with reference to FIG. 2A. If the ITD 20 comprises a unitary structure containing both the RSA 30 and the TU 40, the ITD 20 may be entirely positioned within a heart chamber. As a further alternative, the PTC 34 may be positioned across the septum 132 separating the LV 102 and the RV 104.

Figure 3A:
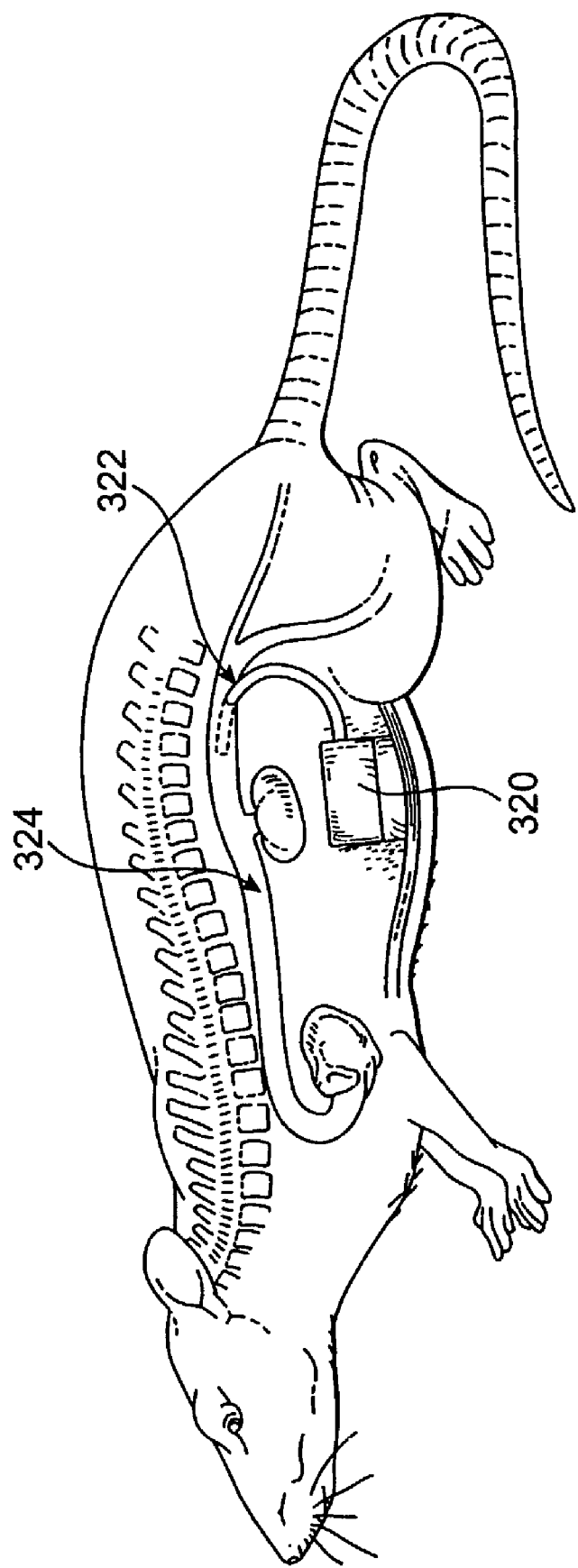
FIG. 3A illustrates a pressure measurement catheter device for measuring blood pressure in the descending aorta of a laboratory animal, according to an embodiment of the invention.
Figure 3B:
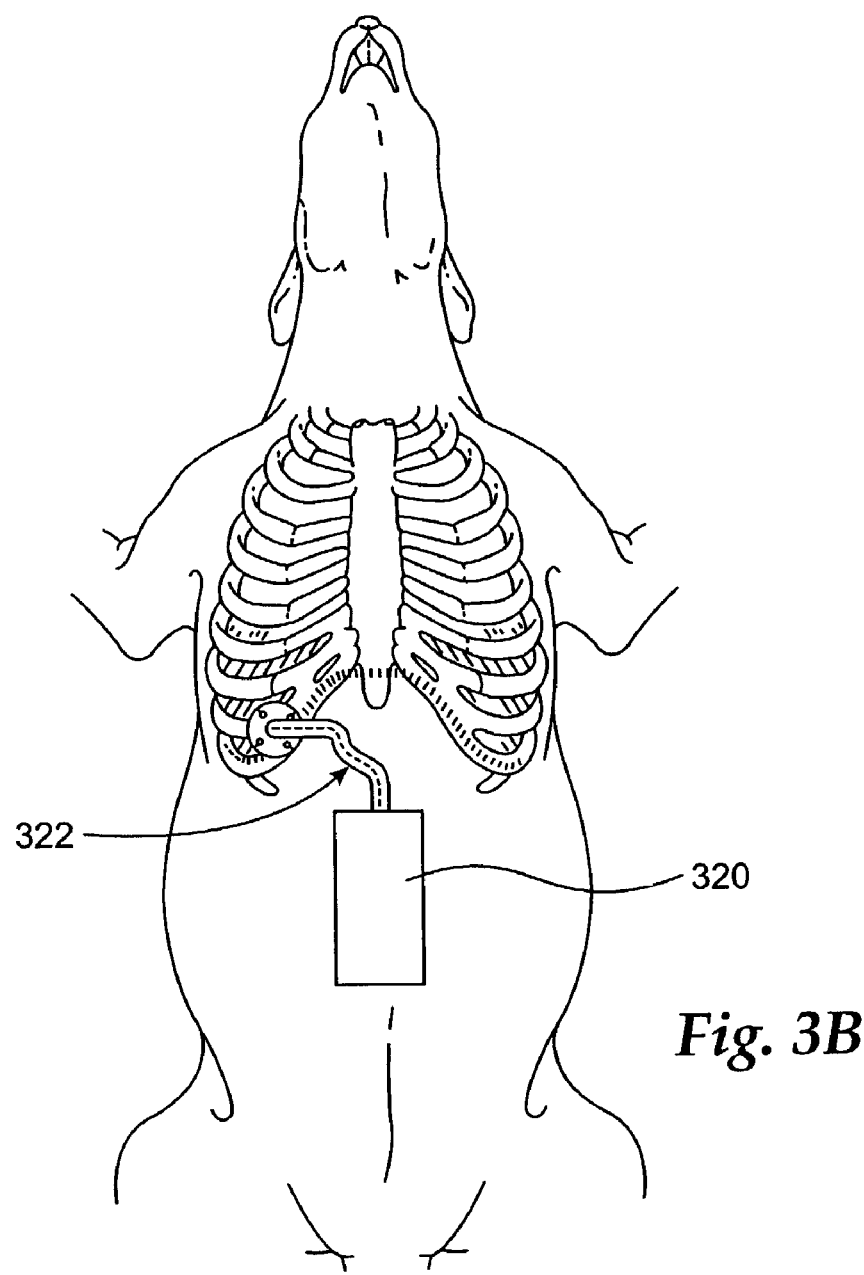
FIGS. 3B and 3C illustrate a pressure measurement catheter device for measuring intrapleural pressure in a laboratory animal, according to an embodiment of the invention.
Figure 3C:
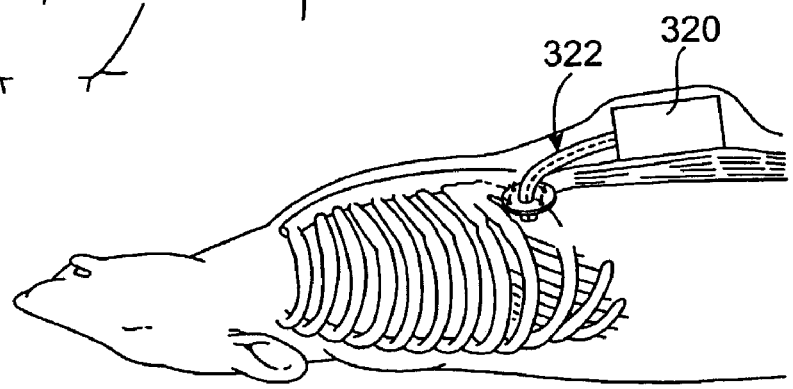
Figure 3D:
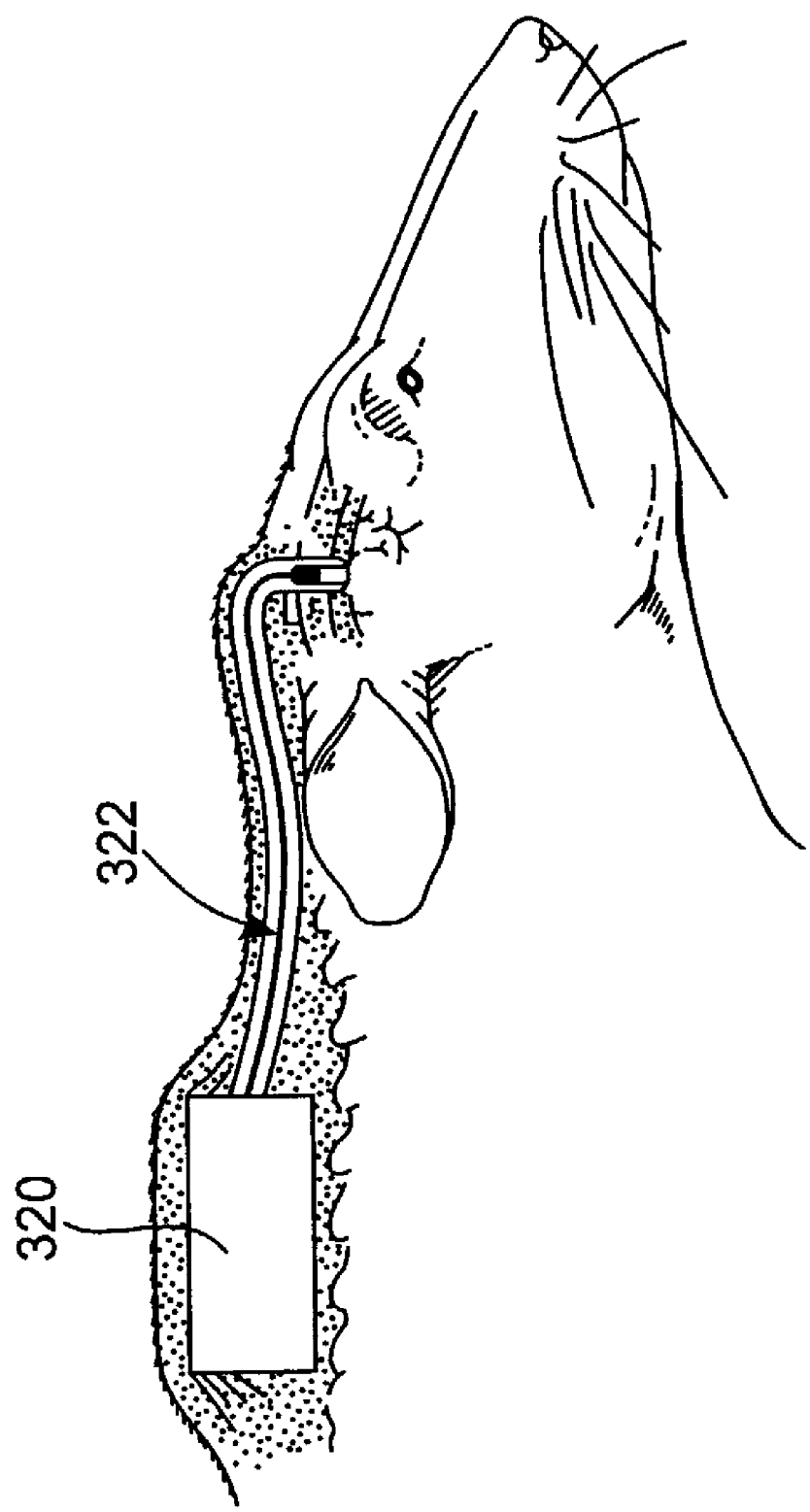
FIG. 3D illustrates a pressure measurement catheter device for measuring intracranial pressure in a laboratory animal, according to an embodiment of the invention.
Figure 4:
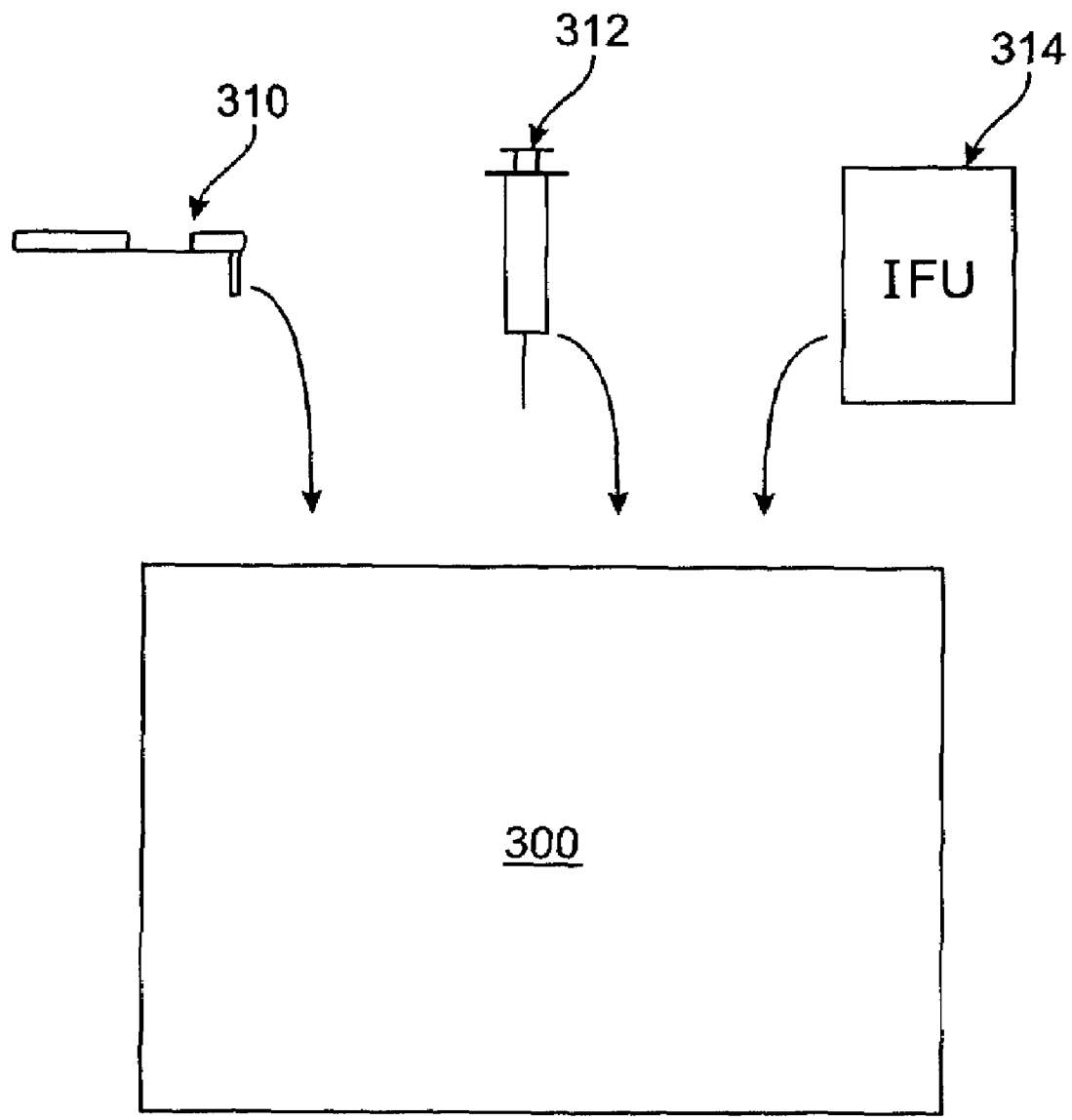
FIG. 4 illustrates a kit including a catheter and a syringe holding viscoelastic barrier material, according to an embodiment of the invention.

With reference now to FIGS. 3A-3D, embodiments of a pressure measurement device 320 are shown in various uses in a laboratory rat for research purposes. These figures emphasize the fact that, although the invention has primarily been described in terms of an embodiment for use in a human heart, other various embodiments may be used in many other animals and settings. As shown in FIG. 3A, for example, a pressure measurement device 320, having a catheter 322, may be used to measure blood pressure in the descending aorta 324 of a laboratory animal. Other embodiments may be used to measure intrapleural pressure in a lab animal, as shown in FIGS. 3B and 3C. And still further embodiments of pressure measurement catheter devices, as shown in FIG. 3D, may be used to measure intracranial pressure in animals in a research context. Many other embodiments of pressure measurement devices and methods for their use are contemplated with the scope of the invention.

Barriers and Methods for Use in Pressure Measurement Catheters

As mentioned above, barriers 26 of the present invention preferably have a combination of characteristics to allow them to be conveniently produced, to be easily placed within a PTC 34, to accurately transmit pressure forces, to be durable over time and/or the like. For example, relatively soft barrier materials are generally used to make barriers 26. Soft barrier materials typically provide for convenient placement of the material into the lumen 36 of the PTC 34 and also tend to minimize hysteresis, which is a delay in transmission of pressure changes. On the other hand, barrier materials are generally chosen so as to not provide an overly soft barrier 26, which would induce significant washout. Washout may be reduced by forming a barrier 26 that is fully cross-linked, nearly fully cross-linked or at least sufficiently cross-linked, so that it has a low solubility fraction. The use of a fully cross-linked barrier 26 also reduces or eliminates permeation of the transmission fluid in the lumen 24 through the barrier 26.

In some embodiments, viscoelastic barrier materials of the present invention, typically used to form a barrier 26 in a PTC 34, are prepared by combining at least one barrier material precursor with an amount of a softener. In other embodiments, two precursor components are combined in approximately a 1:1 ratio, without a softener, to produce a fully cross-linked viscoelastic barrier material having certain softness characteristics described more fully below. Once prepared, the barrier material may then be placed with the lumen 24 of the catheter body 22 in a desired location to form the barrier 26. In some embodiments, for example, the barrier material is injected into the lumen 24, at or near the distal end of the catheter body 22, with a hand syringe. In other embodiments, a machine-powered syringe or other placement device may be used to place barrier materials in the lumen 24.

Any of a number of different barrier material precursors may be used in various embodiments of the invention. In some embodiments, for example, the precursor is formed by combining two components: a liquid polymer having a catalyst and a liquid polymer having a cross-linker. Some barrier material precursors, if cured, would form what is commonly called a gel. For example, cured precursors may form a dimethyl silicone gel, a fluorinated silicone gel, a phenyl silicone gel, another silicone gel or the like. Such gels may be of medical grade, engineering grade or the like. In various embodiments of the present invention, however, an amount of a softener is added to the barrier material precursor before curing, to provide a viscoelastic barrier material with a desired softness. Any suitable softener may be used, such as but not limited to dimethyl silicone oil, fluorinated silicone oil, phenyl silicone oil, another type of silicone oil, a non-silicone oil such as mineral oil, vegetable oil or the like. As discussed further below, the softener may be combined with the barrier material precursor in any suitable amount or ratio to produce a viscoelastic barrier material having a desired softness and/or having other desired characteristics. In one embodiment, for example, dimethyl silicone oil is combined with the barrier material precursor in an amount of about 35% to about 50% by weight, and more preferably between about 40% and about 45% by weight, based on the total weight of the final viscoelastic barrier material.

In one embodiment, the barrier material precursor of the viscoelastic barrier material is a fully cross-linked substance formed by combining at least two monoethylenically or polyethylenically unsaturated monomers. As discussed above, if the precursor were cured without adding a softener, it would obtain properties of a fully cross-linked gel. The degree or percentage of cross-linking is defined as the weight percent of the monomers which have reacted to cross-link at the end of the cross-linking reaction. Thus, a percentage of 100% means that all available monomers are cross-linked. Such complete cross-linking typically requires that the monomeric constituents be combined at a weight or molar ratio to assure that all ethylenically unsaturated binding sites are reacted. For the purposes of this application, the phrase "fully cross-linked" means that at least about 90% of all monomeric constituents or other constituents in a substance which are capable of cross-linking are actually cross-linked. Thus, a substance with about 90% to about 100% of cross-linked monomers is fully cross-linked. The phrase "nearly fully cross-linked" means that between about 70% and about 90% of all monomeric constituents or other constituents in a substance which are capable of cross-linking are actually cross-linked. "Substantially cross-linked" may be defined as between about 50% and about 70% cross-linked and "sufficiently cross-linked" may be defined as between about 25% and about 50% cross-linked. In various embodiments, viscoelastic barrier materials of the present invention may sufficiently, substantially, nearly fully or fully cross-linked and still provide one or more desired characteristics of a barrier material.

It should be emphasized that barrier material precursors and viscoelastic barrier materials of the present invention typically include substances which do not cross link. For example, barrier materials usually include "extractables" which do not cross-link with monomeric constituents. However, the terms defined above for describing levels of cross-linking are based on the percentage of a material's cross-linkable constituents which are cross-linked, not on the percentage of extractables or similar non-cross-linking constituents. For example, a barrier material may include about 70% monomers which are capable of cross-linking and 30% extractables. If 100% of the monomers are cross-linked, then the barrier material is "fully cross-linked," despite the fact that 30% of the overall material comprises extractables.

In addition to controlling the relative amounts (ratio) of the starting monomers, the characteristics and cross-linking of the barrier material precursor may be adjusted by controlling various parameters and process conditions. The polymerization conditions can be selected and adjusted as a means of controlling the percentage of cross-linking and consequently the softness and stability characteristics of the precursor. For example, proper selection of the cross-linking means, the amount and type of cross-linking agent (if any), and the amount and type of the monomer starting materials are means of attaining such control. Certain polymerization conditions may also be varied to such effect, including temperature, degree of ionizing radiation where used, degree of agitation and any other factors affecting the rate and percentage of completion of the polymerization reaction.

As has been discussed above, it is often desirable to have a relatively soft, viscoelastic barrier material that is fully or nearly fully cross-linked. It has been found that various combinations of barrier material precursors and softeners produce such soft, fully cross-linked viscoelastic barrier materials, which may be used to form a barrier in a PTC 34. One way to enhance softness of a barrier material is to limit the amount of extractable materials that include functional groups. As mentioned above, extractables are constituent parts of a barrier material precursor, softener or both that do not cross-link with the monomeric constituents of the barrier material. If extractables contain functional groups, however, they may cross-link sometime after a gel is formed, possibly making the gel difficult to place in a catheter or hindering the performance of the gel. Methods of the present invention typically involve forming a barrier material precursor with sufficient softness such that a relatively small quantity of softener is required. Furthermore, softeners are typically non-functional, so that cross-linking of extractables is minimized.

Generally, viscoelastic barrier materials of the present invention are too soft (or liquid) to allow their softness to be measured. Softness of a barrier material may be indirectly tested, however, by measuring penetration of a barrier material precursor to be used in forming the barrier material. To measure penetration of a precursor, the precursor may be cured or otherwise processed to form a gel-like substance and the gel's penetration properties may then be tested with a standard penetrometer. For example, a penetrometer may be adapted with a foot coupled with a rod, for penetrating a barrier precursor material in a container. In one such device, the foot and rod together weigh approximately 12 grams and the foot is disc-shaped and measures approximately 1 inch in diameter. In a test using the device, a jar containing about 100 g of prepared, cured barrier precursor (gel) is positioned so as to just contact the foot. The foot is then allowed to drop into the gel for ten seconds and the distance that it drops is measured on the rod attached to the foot. In one embodiment of the invention, for example, a 100 g jar of barrier material precursor, when fully cross-linked, has a penetration range at ten seconds of between about 10 mm and about 45 mm and preferably between about 20 mm and about 40 mm and even more preferably between about 21 mm and about 37 mm at a temperature of about 25° C. In one embodiment, a range of penetration measurements is slightly higher at a higher temperature. For example, the barrier material precursor may have a penetration range at ten seconds of between about 15 mm and about 50 mm and preferably between about 25 mm and about 45 mm and even more preferably between about 30 mm and about 37 mm at a temperature of about 37° C. Other testing conditions and/or gels may produce different results but may also represent suitable barrier material precursors for use in forming a viscoelastic barrier material.

As previously discussed, various embodiments of the present invention typically involve combination of at least one barrier material precursor with an amount of a softener to provide a viscoelastic barrier material. A softener and precursor are combined and then cured to produce a viscoelastic barrier material that is typically too soft to be measured with a penetrometer. Thus, it should be emphasized that the penetration test described above is performed on a barrier material precursor without softener. This is an indirect test, used to generally assess how soft a viscoelastic barrier material will be when made from a given barrier material precursor.

As mentioned previously, any suitable barrier material precursor may be used in various embodiments of the present invention. In one embodiment, for example, a dimethyl silicone gel precursor is used. One such barrier material precursor is NuSil Gel-8000, provided by NuSil Silicone Technology (Carpinteria, Calif.; www.nusil.com). In other embodiments, other NuSil gels may also be used, such as MED-6300, MED3-6300, MED5-6300, MED10-6300, MED12-6300 or the like, or gels provided by other manufacturers may be used as precursors. Generally, constituent parts of the barrier material precursor are combined (described below), an amount of a softener is then added, and the mixture is cured to form a viscoelastic barrier material. In one embodiment, the softener is dimethyl silicone oil, although other softeners such as fluorinated silicone oil, phenyl silicone oil, mineral oil, vegetable oil or the like may be used in alternate embodiments. In one embodiment, the silicone oil is combined with the NuSil gel in an amount of about 25% to about 45% silicone oil by weight, compared to the total weight of the finished viscoelastic barrier material, and preferably about 40% to about 45% by weight and even more preferably about 42% by weight. Once the precursor and oil are combined, the combination is cured and allowed to cool to form the finished viscoelastic barrier material, which may then be placed in a pressure measurement catheter.

Typically, precursors such as NuSil Gel-8000 are provided as two constituent parts, both of which are in liquid form—Part A and Part B. Part A is generally a liquid polymer having a catalyst, and Part B is a liquid polymer having a cross-linker. A quantity of Part A is typically measured first and then an approximately equal quantity, by weight, of Part B is combined with Part A until a desired total measurement is reached. In one embodiment, for example, 35 g of Part B is mixed with 35 g of Part A to reach a total measurement of 70 g. Of course, other equal amounts of A and B may be used to form an approximately 1:1 ratio combined gel. If the Part A/Part B 1:1 combination is cured, it generally forms a soft, fully cross-linked gel. As described above, however, some embodiments of the present invention generally involve combining the precursor (i.e., the A/B combination) with a softener before curing. In other embodiments, on the other hand, the A/B combination, in a 1:1 ratio may provide a sufficiently soft, sufficiently cross-linked viscoelastic barrier material so that it may not be desired to add a softener.

After preparing the Part A/Part B precursor, any suitable softening agent, such as a silicone oil, other oil or other agent, may be added in a desired ratio. In one embodiment, MED-361, a dimethyl silicone oil having a viscosity of about 12,500 cps (also available from NuSil Silicon Technology), may be used. In other embodiments, other oils with different viscosities may be used, such as another dimethyl silicone oil, MED-360. A silicone oil may be added to the barrier material precursor in any suitable amount, such as between about 25% and about 45% by weight in one embodiment. Although the method just described includes first combining part A with part B and then combining silicone oil, this order is not required in all embodiments. Various other methods for combining at least one barrier material precursor with an amount of softener are contemplated within the scope of the invention.

In one embodiment, while combining part A, part B and softener, the combination is continuously mixed, such as by an electric mixer. After combining part A, part B and silicone oil, the combination is typically de-gassed, by applying vacuum, centrifuging or any other de-gassing method. For example, the barrier gel may be centrifuged for two minutes at 1000 revolutions per minute. Next, the de-gassed substance is typically cured via heat. For example, curing may entail heating the gel in an oven for four hours at 150 degrees C. Again, various steps may be added to or subtracted from this method, the order of steps may be changed and/or the details of specific steps may be altered without exceeding the scope of the present invention. It has been found that the above-described combination of NuSil Gel-8000 and about 25-45% silicone oil provides a viscoelastic barrier material having many of the advantageous properties described above.

Once a viscoelastic barrier material has been prepared, it may be placed by any suitable means in a desired location within a PTC 34 or similar device. For example, barrier material is often injected into a catheter, using a syringe. The viscoelastic consistency of the barrier materials of the present invention typically allows them to be injected into lumen 24 of a catheter body 22 using a hand-powered syringe. This is an advantage over some prior gel substances which require injection via a power syringe. Placement, amounts, configurations and the like of viscoelastic barrier materials and catheters are described in further detail above, in the description of an exemplary pressure measurement device.

Various properties of barrier materials prepared using the above-described method have been tested in several in vitro and in vivo experiments. The following examples highlight some of the results of those experiments.

EXAMPLE 1

Material Stability Testing

The purpose of this investigation was to measure viscosity of NuSil Gel-8000, prepared in 1:1 ratio and combined with 42% MED-361 silicone oil at 12,500 cps, by weight, at room temperature (~25° C.) and body temperature (~37° C.) over the course of a year. Certain measures of viscosity, such as change in viscosity over time measured as standard deviation from an average viscosity, may correlate with stability of a barrier material.

First, NuSil Gel-8000 was prepared in a 1:1 ratio of 35 g(+/−0.1 g) of part A to 35 g(+/−0.1 g) of part B, and the combination was mixed with an electric mixer set to 10, for ten minutes. MED-361 silicone oil at 12,500 cps was then added to the 70 g(+/−0.1 g)Gel-8000, in an amount of 42% by weight, or 29.4 g(+/−0.1 g), to form a total weight for the combined substance of 99.4 g(+/−0.1 g). The combined substance was then placed in a conventional centrifuge and centrifuged at 1000 rpm for two minutes. Immediately or soon after centrifuging, the combination was placed in an oven set at 150° C. for four hours, and was then left in the oven to cool overnight, to produce a final viscoelastic barrier material. Comparison barrier materials were prepared using the same method, but using 40% or 45% MED-361 silicone oil by weight.

Multiple samples of barrier materials were prepared and viscosity of the barrier materials was then tested using a Brookfield programmable DV-II+ digital viscometer, which is well known to those skilled in the art for measuring viscosity in relatively low-viscosity fluids. Once the barrier materials samples were mixed, cured and cooled, they were tested on the viscometer at room temperature (between about 16° C. and about 25° C.) prior to moving any of the samples to their final yearlong storage space. The sample barrier materials were either stored in the incubator at approximately 37° C. or at room temperature, which varied (again between about 16° C. and about 25° C.).

The viscosity of Gel-8000 mixed with 40%, 42% or 45% MED-361 silicone oil at 12,500 cps in both the room and body temperature scenarios decreased with increasing silicone oil volume. The viscosity range for all samples stored in an incubator was from about 5600 cps to about 7100 cps. The standard deviations of the viscosities of the gel samples from an average viscosity were 164.67 cps (40% oil), 86.59 cps (42% oil) and 225.79 cps (45% oil). A relatively narrow range of viscosities of a barrier material over time may be indicative of a stable barrier material. Such stability likely correlates with a fully cross-linked, or nearly fully cross-linked, barrier material. It is believed that the ranges and standard deviations measured for the NuSil Gel-8000/MED-361 silicone oil barrier materials indicate a relatively stable barrier material, possibly as stable as or more stable than other currently available gels.

EXAMPLE 2

Barrier Washout Testing

The purpose of this investigation was to establish a washout range in vitro with the NuSil Gel-8000/MED-361 silicone oil, prepared as described above. Barrier material was placed in several pressure transmission catheter devices to form barriers and washout (or "recession") was measured at 0, 2, 4 and 6 weeks. For comparison, a number of catheters were prepared with Dow Q7-2218 gel, prepared off ratio at between about 1.65:1 and about 1.90:1 to provide sufficient softness and having no silicone oil added. The Harvard Pulsatile Blood Pump™ was used to simulate the ventricular action of the heart through the manipulation of the flow rate. A water and glycerol solution was used to replicate the viscosity of blood.

Every two weeks, at 0, 2, 4 and 6 weeks, barrier recession and length was measured in each transmitter with a ruler, reticule and microscope. (Barrier recession was measured with the reticule and barrier length with the ruler.) The Harvard Pulsatile Pump™ was stopped at the beginning of washout measurements and turned back on once all the measurements were taken. In order to measure the barrier recession, each of the transmitters had to be removed from the flow loop one at a time to manipulate the catheter and observe the barrier recession. Once a measurement was taken, the transmitter was returned to the flow loop.

Overall, the combination of Gel-8000 and 42% MED-361 silicone oil had the lowest amount of washout during the six-week study. For example, in one transmitter, this gel had a washout measurement of 0.42 mm after six weeks. The measured washout rates for all NuSil Gel-8000/MED-361 gel combinations are believed to be comparable or superior to washout rates for currently available gels. Similar washout studies were performed in vivo, using laboratory mice. Results at 3 months were: Dow off-ratio gel washout of about 0.75 mm and NuSil barrier washout of about 0.63 with 40% oil, 0.50 mm with 42% oil and 0.56 mm with 45% oil.

As is evident from the foregoing description, various embodiments of the present invention provide for viscoelastic barrier materials and/or barriers 26 for use in PTCs 34 that have one or more advantageous properties. For example, many viscoelastic barrier materials of the present invention generally are filly or nearly fully cross-linked, as measured by changes in viscosity over time. This level of cross-linking tends to reduce washout rates and enhance stability of the a barrier 26. Barrier materials of the invention also typically have a desirable softness, as measured by penetration value of the barrier material precursors. Softness generally allows for easy handling of the materials and easy placement within the lumen 24 of a catheter body 22. A relatively soft barrier may also enhance the accuracy of pressure measurement by limiting hysteresis. Furthermore, component parts of a barrier material precursor in some embodiments of the invention are combined in a 1:1 ratio, which enhances consistency between batches and may provide enhanced stability of the barrier material. Barrier materials and softeners of the present invention also have relatively few, if any, extractables with functional groups, so the extractables generally do not cross-link after preparation of the material.

The above description has focused on one exemplary embodiment of a viscoelastic barrier material in which a barrier material precursor, NuSil Gel-8000, is combined with a dimethyl silicone oil softener in a ratio of between about 25% and about 45% by weight of softener to the total weight of the finished barrier material. It should be emphasized again, however, that this is merely one possible embodiment and that any other suitable combination of at least one barrier material precursor with an amount of a softener may be used in various alternative embodiments.

Referring now to FIG. 3, a kit 300 according to one embodiment of the present invention suitably includes a catheter 310 or similar implantable device, a syringe 312 containing an amount of viscoelastic barrier material and instructions for use (IFU) 314. In some embodiments, only catheter 310 and IFU 314 may be provided. The extra barrier material with syringe 312 may be provided in the same kit 300 or in a separate kit with different IFU. This extra barrier material may be used, for example, to refill the lumen 24 of the catheter 310 if a portion of barrier material is inadvertently removed when the protective tip is removed from the catheter 310. Alternatively, a user may wish to refill the catheter 310 before placing into a second test subject, such as a laboratory animal, if the catheter 310 is reusable. In some embodiments, catheter 310 will be included in kit 300 completely ready to use. In other embodiments, a physician or other user may inject or otherwise place barrier material in the lumen 24 of the catheter 310 before use. Instructions for use 314 may include, but are not limited to, instructions for making a pressure measurement catheter, for refilling a catheter and/or for using the catheter in a human patient, laboratory animal, in vitro testing device or other setting.

While the invention has been shown and described with reference to embodiments thereof, various changes in form and detail may be made without departing from the spirit and scope of the invention as described in the following claims. The above description, therefore, is for exemplary purposes only and should not be interpreted to limit the scope of the invention as defined in the claims.

What is claimed is:

1. A pressure measurement catheter comprising a lumen containing a viscoelastic barrier material, the viscoelastic barrier material including at least one viscoelastic barrier material precursor combined with an amount of a softener;
    wherein the viscoelastic barrier material has a viscosity of between about 5600 cps and about 7100 cps in an environment having a temperature of about 37° C.

2. A pressure measurement catheter as in claim 1, wherein the softener comprises dimethyl silicone oil.

3. A pressure measurement catheter comprising a lumen containing a viscoelastic barrier material, the viscoelastic barrier material including a cross-linked silicone gel and a softener within the gel.

4. The pressure measurement catheter of claim 3, wherein the cross-linked silicone gel is formed by combining,
    (a) a first liquid silicone polymer comprising a catalyst, and
    (b) a second liquid silicone polymer comprising a cross-linker.

5. The pressure measurement catheter of claim 3, wherein the viscoelastic barrier material is fully cross-linked.

6. The pressure measurement device of claim 3, wherein the softener comprises an oil.

7. The pressure measurement device of claim 3, wherein the softener is selected from the group consisting of dimethyl silicone oil, fluorinated silicone oil, phenyl silicone oil, mineral oil, vegetable oil, and combinations thereof.

8. The pressure measurement device of claim 3, wherein the softener comprises dimethyl silicone oil.

9. The pressure measurement device of claim 3, wherein the viscoelastic barrier material comprises between 35 and 50 weight percent softener.

10. The pressure measurement device of claim 3, wherein the viscoelastic barrier material comprises between 40 and 45 weight percent softener.

11. The pressure measurement device of claim 3, wherein the viscoelastic barrier material comprises between 25 to 45 weight percent softener.

12. The pressure measurement device of claim 3, wherein the gel is selected from the group consisting of a dimethyl silicone gel, a fluorinated silicone gel, a phenyl silicone gel, and combinations thereof.

13. The pressure measurement device of claim 3, wherein the viscoelastic barrier material has a penetration range at ten seconds of between about 21 mm and about 37 mm at a temperature of about 25° C., wherein the penetration range is measured in a container of about 100 g of the viscoelastic barrier material, using a penetrometer having a foot and rod, the foot having a 1-inch diameter and the foot and rod weighing about 12 g.

14. The pressure measurement device of claim 3, wherein the viscoelastic barrier material has a penetration range at ten seconds of between about 30 mm and about 37 mm at a temperature of about 37° C., wherein the penetration range is measured in a container of about 100 g of the viscoelastic barrier material, using a penetrometer having a foot and rod, the foot having a 1-inch diameter and the foot and rod weighing about 12 g.

15. The pressure measurement device of claim 3, wherein the viscoelastic barrier material has a viscosity of between about 5200 cps and about 10,100 cps in an environment having a temperature of about 25° C.

16. The pressure measurement device of claim 3, wherein the viscoelastic barrier material has a viscosity of between about 5600 cps and about 7100 cps in an environment having a temperature of about 37° C.

17. The pressure measurement device of claim 3, wherein the viscoelastic barrier material has a viscosity that changes by less than about 1,000 cps during a period of one year in an environment having a temperature of between about 16° and about 25° C.

18. The pressure measurement device of claim 3, wherein the viscoelastic barrier material has a viscosity that changes by less than about 500 cps during a period of one year in an environment having a temperature of between about 35° and about 40° C.

19. A pressure measurement catheter comprising a lumen containing a viscoelastic barrier material, the viscoelastic barrier material including a cross-linked dimethyl silicone gel and between 35 and 50 weight percent dimethyl silicone oil within the gel.

20. A pressure measurement device comprising an implantable telemetry device comprising a viscoelastic barrier material, the viscoelastic barrier material comprising a cross-linked silicone gel and a softener within the gel.

21. A pressure measurement catheter comprising a lumen containing a viscoelastic barrier material, the viscoelastic barrier material including a fully cross-linked silicone gel, the viscoelastic barrier material having a penetration range at ten seconds of between about 21 mm and about 37 mm at a temperature of about 25° C., wherein the penetration range is measured in a container of about 100 g of the viscoelastic barrier material, using a penetrometer having a foot and rod, the foot having a 1-inch diameter and the foot and rod weighing about 12 g.

22. The pressure measurement device of claim 21, wherein the viscoelastic barrier material has a penetration range at ten seconds of between about 30 mm and about 37 mm at a temperature of about 37° C., wherein the penetration range is measured in a container of about 100 g of the viscoelastic barrier material, using a penetrometer having a foot and rod, the foot having a 1-inch diameter and the foot and rod weighing about 12 g.

23. A pressure measurement catheter comprising a lumen containing a viscoelastic barrier material, the viscoelastic barrier material including a fully cross-linked silicone gel, the viscoelastic barrier material having a viscosity of between about 5200 cps and about 10,100 cps in an environment having a temperature of about 25° C.

24. The pressure measurement device of claim 23, wherein the viscoelastic barrier material has a viscosity of between about 5600 cps and about 7100 cps in an environment having a temperature of about 37° C.

25. The pressure measurement device of claim 23, wherein the viscoelastic barrier material has a viscosity that changes by less than about 1,000 cps during a period of one year in an environment having a temperature of between about 16° and about 25° C.

26. The pressure measurement device of claim 23, wherein the viscoelastic barrier material has a viscosity that changes by less than about 500 cps during a period of one year in an environment having a temperature of between about 35° and about 40° C.

27. A method of making a pressure measurement catheter, the method comprising:
providing a pressure measurement catheter having a proximal end, a distal end and a lumen;
providing a viscoelastic barrier material comprising a cross-linked silicone gel and a softener within the gel; and
placing the viscoelastic barrier material in the lumen near the distal end of the catheter.

28. The method of claim 27, wherein providing the viscoelastic barrier material comprises mixing
(a) a first liquid silicone polymer comprising a catalyst,
(b) a second liquid silicone polymer comprising a cross-linker, and
(c) the softener.

29. The method of claim 28, wherein the softener is added after mixing the first and second silicone polymers.

30. The method of claim 29, wherein the viscoelastic barrier material is cured after adding the softener to fully cross-link the viscoelastic barrier material.

31. The method of claim 27, wherein the softener comprises an oil.

32. The method of claim 27, wherein the softener is selected from the group consisting of dimethyl silicone oil, fluorinated silicone oil, phenyl silicone oil, mineral oil, vegetable oil, and combinations thereof.

33. The method of claim 27, wherein the softener comprises dimethyl silicone oil.

34. The method of claim 27, wherein the viscoelastic barrier material comprises between 35 and 50 weight percent softener.

35. The method of claim 27, wherein the viscoelastic barrier material comprises between 40 and 45 weight percent softener.

36. The method of claim 27, wherein the viscoelastic barrier material comprises between 25 to 45 weight percent softener.

37. The method of claim 27, wherein the gel is selected from the group consisting of a dimethyl silicone gel, a fluorinated silicone gel, a phenyl silicone gel, and combinations thereof.

38. The method of claim 27, wherein the viscoelastic barrier material has a penetration range at ten seconds of between about 21 mm and about 37 mm at a temperature of about 25° C., wherein the penetration range is measured in a container of about 100 g of the viscoelastic barrier material, using a penetrometer having a foot and rod, the foot having a 1-inch diameter and the foot and rod weighing about 12 g.

39. The method of claim 27, wherein the viscoelastic barrier material has a penetration range at ten seconds of between about 30 mm and about 37 mm at a temperature of about 37° C., wherein the penetration range is measured in a container of about 100 g of the viscoelastic barrier material, using a penetrometer having a foot and rod, the foot having a 1-inch diameter and the foot and rod weighing about 12 g.

40. The method of claim 27, wherein the viscoelastic barrier material has a viscosity of between about 5200 cps and about 10,100 cps in an environment having a temperature of about 25° C.

41. The method of claim 27, wherein the viscoelastic barrier material has a viscosity of between about 5600 cps and about 7100 cps in an environment having a temperature of about 37° C.

42. The method of claim 27, wherein the viscoelastic barrier material has a viscosity that changes by less than about 1,000 cps during a period of one year in an environment having a temperature of between about 16° and about 25° C.

43. The method of claim 27, wherein the viscoelastic barrier material has a viscosity that changes by less than about 500 cps during a period of one year in an environment having a temperature of between about 35° and about 40° C.

44. The method of claim 27, wherein placing the viscoelastic barrier material comprises injecting the material into the lumen using a handheld syringe.

45. The method of claim 27, wherein placing the viscoelastic barrier material comprises refilling a portion of the lumen with the material.

46. A method of making a pressure measurement catheter, the method comprising:
   providing a pressure measurement catheter having a proximal end, a distal end and a lumen;
   providing a viscoelastic barrier material comprising a fully cross-linked silicone gel, the viscoelastic barrier material having a penetration range at ten seconds of between about 21 mm and about 37 mm at a temperature of about 25° C., wherein the penetration range is measured in a container of about 100 g of the viscoelastic barrier material, using a penetrometer having a foot and rod, the foot having a 1-inch diameter and the foot and rod weighing about 12 g; and
   placing the viscoelastic barrier material in the lumen near the distal end of the catheter.

47. The method of claim 46, wherein the viscoelastic barrier material has a penetration range at ten seconds of between about 30 mm and about 37 mm at a temperature of about 37° C., wherein the penetration range is measured in a container of about 100 g of the viscoelastic barrier material, using a penetrometer having a foot and rod, the foot having a 1-inch diameter and the foot and rod weighing about 12 g.

48. A method of making a pressure measurement catheter, the method comprising:
   providing a pressure measurement catheter having a proximal end, a distal end and a lumen;
   providing a viscoelastic barrier material comprising a fully cross-linked silicone gel, the viscoelastic barrier material having a viscosity of between about 5200 cps and about 10,100 cps in an environment having a temperature of about 25° C.; and
   placing the viscoelastic barrier material in the lumen near the distal end of the catheter.

49. The method of claim 48, wherein the viscoelastic barrier material has a viscosity of between about 5600 cps and about 7100 cps in an environment having a temperature of about 37° C.

50. The method of claim 48, wherein the viscoelastic barrier material has a viscosity that changes by less than about 1,000 cps during a period of one year in an environment having a temperature of between about 16° and about 25° C.

51. The method of claim 48, wherein the viscoelastic barrier material has a viscosity that changes by less than about 500 cps during a period of one year in an environment having a temperature of between about 35° and about 40° C.

* * * * *